(12) United States Patent
Weidman et al.

(10) Patent No.: US 10,653,567 B2
(45) Date of Patent: *May 19, 2020

(54) INCONTINENCE DETECTION PAD VALIDATION APPARATUS AND METHOD

(71) Applicant: Hill-Rom Services, Inc., Batesville, IN (US)

(72) Inventors: Bryan Weidman, Columbus, IN (US); Gavin M. Monson, Oxford, OH (US); John D. Christie, Batesville, IN (US); James D. Voll, Columbus, IN (US)

(73) Assignee: Hill-Rom Services, Inc., Batesville, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/040,816

(22) Filed: Jul. 20, 2018

(65) Prior Publication Data

US 2018/0325744 A1 Nov. 15, 2018

Related U.S. Application Data

(63) Continuation-in-part of application No. 15/596,036, filed on May 16, 2017, now Pat. No. 10,350,116,
(Continued)

(51) Int. Cl.
*A61F 13/42* (2006.01)
*A61F 13/514* (2006.01)
(Continued)

(52) U.S. Cl.
CPC ........ *A61F 13/42* (2013.01); *A61F 13/51498* (2013.01); *A61G 7/00* (2013.01);
(Continued)

(58) Field of Classification Search
CPC ...................................................... A61F 13/42
See application file for complete search history.

(56) References Cited

U.S. PATENT DOCUMENTS 1,772,232 A 8/1930 Guilder
2,127,538 A 8/1938 Seiger
(Continued)

FOREIGN PATENT DOCUMENTS

CA 2361145 A1 12/1999
CA 2494896 A1 12/1999
(Continued)

OTHER PUBLICATIONS

Extended European Search Report dated Jul. 16, 2018 for European Patent Application No. 16866993.5; 8 pages total.
(Continued)

*Primary Examiner* — Nabil H Syed
*Assistant Examiner* — Cal J Eustaquio
(74) *Attorney, Agent, or Firm* — Barnes & Thornburg LLP

(57) ABSTRACT

An incontinence detection pad has an RFID tag in which an authentication code, such as an electronic product code (EPC), is stored. A reader in wireless communication with the RFID tag of the incontinence detection pad verifies that the incontinence detection pad is an authorized detection pad. Thus, unauthorized incontinence detection pads that do not have the proper authentication code are not able to be used in an incontinence detection system.

29 Claims, 12 Drawing Sheets

Related U.S. Application Data which is a continuation-in-part of application No. PCT/US2016/062167, filed on Nov. 16, 2016.

(60) Provisional application No. 62/255,592, filed on Nov. 16, 2015.

(51) Int. Cl.
*A61G 7/00* (2006.01)
*G06K 7/10* (2006.01)
*A61G 7/05* (2006.01)
*A61F 13/84* (2006.01)
*A61F 13/15* (2006.01)

(52) U.S. Cl.
CPC ............ *A61G 7/05* (2013.01); *G06K 7/10366* (2013.01); *A61F 2013/15154* (2013.01); *A61F 2013/424* (2013.01); *A61F 2013/8482* (2013.01); *A61G 2203/20* (2013.01); *A61G 2203/30* (2013.01); *A61G 2205/60* (2013.01)

(56) References Cited

U.S. PATENT DOCUMENTS

| | | |
|---|---|---|
| 2,644,050 A | 6/1953 | Seiger |
| 2,668,202 A | 2/1954 | Kaplan |
| 2,726,294 A | 12/1955 | Kroening et al. |
| 2,907,841 A | 10/1959 | Campbell |
| 3,199,095 A | 8/1965 | Ashida |
| 3,971,371 A | 7/1976 | Bloom |
| 4,069,817 A | 1/1978 | Fenote et al. |
| 4,106,001 A | 8/1978 | Mahoney |
| 4,163,449 A | 8/1979 | Regal |
| 4,191,950 A | 3/1980 | Levin et al. |
| 4,212,295 A | 7/1980 | Snyder |
| 4,228,426 A | 10/1980 | Roberts |
| 4,347,503 A | 8/1982 | Uyehara |
| 4,539,559 A | 9/1985 | Kelley et al. |
| 4,747,166 A | 5/1988 | Kuntz |
| 4,965,554 A | 10/1990 | Darling |
| 5,081,422 A | 1/1992 | Shih |
| 5,086,294 A | 2/1992 | Schwab, Jr. |
| 5,137,033 A | 8/1992 | Norton |
| 5,144,284 A | 9/1992 | Hammett |
| 5,291,181 A | 3/1994 | De Ponte |
| 5,438,721 A | 8/1995 | Pahno et al. |
| 5,459,452 A | 10/1995 | DePonte |
| 5,491,609 A | 2/1996 | Dankman et al. |
| 5,537,095 A | 7/1996 | Dick et al. |
| 5,675,854 A | 10/1997 | Zibelin |
| 5,760,694 A | 6/1998 | Nissim |
| 5,790,035 A | 8/1998 | Ho |
| 5,824,883 A | 10/1998 | Park et al. |
| 5,910,080 A | 6/1999 | Selton |
| 5,947,943 A | 9/1999 | Lee |
| 6,028,241 A | 2/2000 | Armstead |
| 6,047,419 A | 4/2000 | Fergusaon |
| 6,104,311 A | 8/2000 | Lastinger |
| 6,292,102 B1 | 9/2001 | Smith |
| 6,340,932 B1 | 1/2002 | Rodgers et al. |
| 6,341,393 B1 | 1/2002 | Votel |
| 6,351,215 B2 | 2/2002 | Rodgers et al. |
| 6,362,737 B1 | 3/2002 | Rodgers et al. |
| 6,384,728 B1 | 5/2002 | Kanor et al. |
| 6,544,200 B1 | 4/2003 | Smith et al. |
| 6,552,661 B1 | 4/2003 | Lastinger et al. |
| 6,583,722 B2 | 6/2003 | Jeutter et al. |
| 6,603,403 B2 | 8/2003 | Jeutter et al. |
| 6,621,410 B1 | 9/2003 | Lastinger et al. |
| 6,639,517 B1 | 10/2003 | Chapman et al. |
| 6,774,800 B2 | 8/2004 | Friedman et al. |
| 6,831,562 B2 | 12/2004 | Rodgers et al. |
| 6,832,507 B1 | 12/2004 | van de Berg et al. |
| 6,876,303 B2 | 4/2005 | Reeder et al. |
| 6,933,849 B2 | 8/2005 | Sawyer |
| 6,948,205 B2 | 9/2005 | Van Der Wurf et al. |
| 6,982,646 B2 | 1/2006 | Rodgers et al. |
| 7,017,213 B2 | 3/2006 | Chisari |
| 7,030,731 B2 | 4/2006 | Lastinger et al. |
| 7,071,830 B2 | 7/2006 | Sahlberg et al. |
| 7,120,952 B1 | 10/2006 | Bass et al. |
| 7,181,206 B2 | 2/2007 | Pedersen |
| 7,250,547 B1 | 7/2007 | Hofmeister et al. |
| 7,253,729 B2 | 8/2007 | Lastinger et al. |
| 7,274,944 B2 | 9/2007 | Lastinger et al. |
| 7,302,278 B2 | 11/2007 | Lastinger et al. |
| 7,305,246 B2 | 12/2007 | Lastinger et al. |
| 7,308,270 B2 | 12/2007 | Lastinger et al. |
| 7,348,930 B2 | 3/2008 | Lastinger et al. |
| 7,349,701 B2 | 3/2008 | Lastinger et al. |
| 7,355,090 B2 | 4/2008 | Ales, III et al. |
| 7,359,675 B2 | 4/2008 | Lastinger et al. |
| 7,400,860 B2 | 7/2008 | Lastinger et al. |
| 7,424,298 B2 | 9/2008 | Lastinger et al. |
| 7,489,252 B2 | 2/2009 | Long et al. |
| 7,489,282 B2 | 2/2009 | Lastinger et al. |
| 7,498,478 B2 | 3/2009 | Long et al. |
| 7,551,089 B2 | 6/2009 | Sawyer |
| 7,586,385 B2 | 9/2009 | Rokhsaz |
| 7,595,734 B2 | 9/2009 | Long et al. |
| 7,595,756 B2 | 9/2009 | Lastinger et al. |
| 7,598,853 B2 | 10/2009 | Becker et al. |
| 7,598,862 B2 | 10/2009 | Lastinger et al. |
| 7,599,699 B2 | 10/2009 | Lastinger et al. |
| 7,616,959 B2 | 11/2009 | Spenik et al. |
| 7,633,378 B2 | 12/2009 | Rodgers et al. |
| 7,649,125 B2 | 1/2010 | Ales, III et al. |
| 7,663,483 B2 | 2/2010 | Spenik et al. |
| 7,667,600 B2 | 2/2010 | Woodbury et al. |
| 7,812,731 B2 | 10/2010 | Bunza et al. |
| 7,822,386 B2 | 10/2010 | Lastinger et al. |
| 7,834,234 B2 | 11/2010 | Roe et al. |
| 7,834,235 B2 | 11/2010 | Long et al. |
| 7,834,765 B2 | 11/2010 | Sawyer |
| 7,834,766 B2 | 11/2010 | Sawyer |
| 7,838,720 B2 | 11/2010 | Roe et al. |
| 7,849,544 B2 | 12/2010 | Flocard et al. |
| 7,873,319 B2 | 1/2011 | Lastinger et al. |
| 7,977,529 B2 | 7/2011 | Bergman et al. |
| 8,009,646 B2 | 8/2011 | Lastinger et al. |
| 8,073,386 B2 | 12/2011 | Pedersen |
| 8,081,043 B2 | 12/2011 | Rokhsaz |
| 8,102,254 B2 | 1/2012 | Becker et al. |
| 8,104,126 B2 | 1/2012 | Caminade et al. |
| 8,106,782 B2 | 1/2012 | Fredriksson et al. |
| 8,111,165 B2 | 2/2012 | Ortega et al. |
| 8,111,678 B2 | 2/2012 | Lastinger et al. |
| 8,121,856 B2 | 2/2012 | Huster et al. |
| 8,181,290 B2 | 5/2012 | Brykalski et al. |
| 8,191,187 B2 | 6/2012 | Brykalski et al. |
| 8,196,809 B2 | 6/2012 | Thorstensson |
| 8,237,572 B2 | 8/2012 | Clement et al. |
| 8,248,249 B2 | 8/2012 | Clement et al. |
| 8,270,383 B2 | 8/2012 | Lastinger et al. |
| 8,279,069 B2 | 10/2012 | Sawyer |
| 8,319,633 B2 | 11/2012 | Becker et al. |
| 8,325,695 B2 | 12/2012 | Lastinger et al. |
| 8,332,975 B2 | 12/2012 | Brykalski et al. |
| 8,345,651 B2 | 1/2013 | Lastinger et al. |
| 8,395,014 B2 | 3/2013 | Helmer et al. |
| 8,428,039 B2 | 4/2013 | Lastinger et al. |
| 8,428,605 B2 | 4/2013 | Pedersen et al. |
| 8,461,982 B2 | 6/2013 | Becker et al. |
| 8,482,305 B2 | 7/2013 | Johnson |
| 8,487,774 B2 | 7/2013 | Reeder et al. |
| 8,502,684 B2 | 8/2013 | Bunza et al. |
| 8,628,506 B2 | 1/2014 | Ales, III et al. |
| 8,674,826 B2 | 3/2014 | Becker et al. |
| 8,742,929 B2 | 6/2014 | Sawyer |
| 8,749,319 B2 | 6/2014 | Rokhsaz et al. |
| 8,766,804 B2 | 7/2014 | Reeder |
| 8,842,013 B2 | 9/2014 | Sawyer |
| 8,855,089 B2 | 10/2014 | Lastinger et al. |
| 8,866,615 B2 | 10/2014 | Sawyer |

(56) References Cited

U.S. PATENT DOCUMENTS

| | | |
|---|---|---|
| 8,878,557 B2 | 11/2014 | Kristiansen et al. |
| 8,878,676 B2 | 11/2014 | Koblasz |
| 8,896,449 B2 | 11/2014 | Sawyer |
| 8,914,923 B2 | 12/2014 | Smith |
| 8,933,292 B2 | 1/2015 | Abraham et al. |
| 8,962,909 B2 | 2/2015 | Groosman et al. |
| 8,978,452 B2 | 3/2015 | Johnson et al. |
| 9,048,819 B2 | 6/2015 | Rokhsaz et al. |
| 9,107,776 B2 | 8/2015 | Bergman et al. |
| 9,160,054 B2 | 10/2015 | Yu et al. |
| 9,323,797 B2 | 4/2016 | Acree |
| 9,366,644 B1 | 6/2016 | Lastinger et al. |
| 9,506,886 B1 | 11/2016 | Woodbury et al. |
| 9,649,230 B1 | 5/2017 | Li |
| 9,719,951 B1 | 8/2017 | Woodbury et al. |
| 2002/0011932 A1 | 1/2002 | Rodgers et al. |
| 2002/0033757 A1 | 3/2002 | Rodgers et al. |
| 2002/0145525 A1 | 10/2002 | Friedman et al. |
| 2002/0145526 A1 | 10/2002 | Friedman et al. |
| 2003/0019405 A1 | 1/2003 | Ballendat |
| 2003/0030568 A1 | 2/2003 | Lastinger et al. |
| 2004/0155754 A1* | 8/2004 | Fischer ............... G06K 19/0701 340/10.34 |
| 2005/0003763 A1 | 1/2005 | Lastinger et al. |
| 2005/0003865 A1 | 1/2005 | Lastinger et al. |
| 2005/0046578 A1 | 3/2005 | Pires |
| 2005/0052282 A1 | 3/2005 | Rodgers et al. |
| 2005/0060246 A1 | 3/2005 | Lastinger et al. |
| 2005/0174246 A1 | 8/2005 | Picco et al. |
| 2005/0242946 A1 | 11/2005 | Hubbard, Jr. et al. |
| 2005/0250453 A1 | 11/2005 | Lastinger et al. |
| 2005/0277441 A1 | 12/2005 | Lastinger et al. |
| 2005/0282545 A1 | 12/2005 | Lastinger et al. |
| 2005/0282553 A1 | 12/2005 | Lastinger et al. |
| 2006/0054681 A1* | 3/2006 | Park ................. G06K 19/07758 235/375 |
| 2006/0164320 A1 | 7/2006 | Lastinger et al. |
| 2006/0270351 A1 | 11/2006 | Lastinger et al. |
| 2007/0018819 A1* | 1/2007 | Streeb ................. G06K 7/0008 340/572.1 |
| 2007/0159332 A1 | 7/2007 | Koblasz |
| 2007/0202809 A1 | 8/2007 | Lastinger et al. |
| 2007/0250603 A1* | 10/2007 | Suen ................... G06F 16/20 709/220 |
| 2007/0270774 A1 | 11/2007 | Bergman et al. |
| 2008/0116990 A1 | 5/2008 | Rokhsaz |
| 2008/0204245 A1 | 8/2008 | Blair et al. |
| 2008/0262376 A1 | 10/2008 | Price |
| 2008/0263776 A1 | 10/2008 | O'Reagan et al. |
| 2008/0300559 A1 | 12/2008 | Gustafson et al. |
| 2009/0160648 A1 | 6/2009 | Rokhsaz |
| 2009/0289743 A1 | 11/2009 | Rokhsaz |
| 2009/0292265 A1 | 11/2009 | Helmer et al. |
| 2009/0315728 A1 | 12/2009 | Ales, III et al. |
| 2009/0326417 A1 | 12/2009 | Ales, III et al. |
| 2010/0043143 A1 | 2/2010 | O'Reagan et al. |
| 2011/0025458 A1 | 2/2011 | Rokhsaz et al. |
| 2011/0025473 A1 | 2/2011 | Rokhsaz et al. |
| 2011/0092890 A1 | 4/2011 | Stryker et al. |
| 2011/0115635 A1 | 5/2011 | Petrovski et al. |
| 2011/0263952 A1 | 10/2011 | Bergman et al. |
| 2011/0283459 A1 | 11/2011 | Essers |
| 2011/0291810 A1 | 12/2011 | Rokhsaz et al. |
| 2011/0295619 A1 | 12/2011 | Tough |
| 2011/0300808 A1 | 12/2011 | Rokhsaz et al. |
| 2011/0302720 A1 | 12/2011 | Yakam et al. |
| 2011/0309937 A1 | 12/2011 | Bunza et al. |
| 2012/0092027 A1 | 4/2012 | Forster |
| 2012/0105233 A1 | 5/2012 | Bobey et al. |
| 2012/0119912 A1 | 5/2012 | Ortega et al. |
| 2012/0130330 A1 | 5/2012 | Wilson et al. |
| 2012/0165772 A1 | 6/2012 | Groosman et al. |
| 2012/0216607 A1 | 8/2012 | Sjöholm et al. |
| 2012/0217311 A1 | 8/2012 | Rokhsaz et al. |
| 2012/0268278 A1 | 10/2012 | Lewis et al. |
| 2012/0300933 A1* | 11/2012 | Baranowski ......... H04L 9/3271 380/270 |
| 2013/0063244 A1* | 3/2013 | Raed .................. B60R 25/24 340/5.8 |
| 2013/0079590 A1 | 3/2013 | Bengtson |
| 2013/0109929 A1 | 5/2013 | Menzel |
| 2013/0123726 A1 | 5/2013 | Yu et al. |
| 2013/0254141 A1 | 9/2013 | Barda et al. |
| 2014/0120836 A1 | 5/2014 | Rokhsaz et al. |
| 2014/0148772 A1 | 5/2014 | Hu et al. |
| 2014/0152442 A1 | 6/2014 | Li |
| 2014/0200538 A1 | 7/2014 | Euliano et al. |
| 2014/0236629 A1 | 8/2014 | Kim et al. |
| 2014/0244644 A1 | 8/2014 | Mashinchi et al. |
| 2014/0247125 A1 | 9/2014 | Barsky |
| 2014/0266735 A1 | 9/2014 | Riggio et al. |
| 2014/0276504 A1 | 9/2014 | Heil et al. |
| 2014/0296808 A1 | 10/2014 | Curran et al. |
| 2014/0358099 A1 | 12/2014 | Durgin et al. |
| 2015/0080819 A1 | 3/2015 | Charna et al. |
| 2015/0080834 A1 | 3/2015 | Mills |
| 2015/0087935 A1 | 3/2015 | Davis et al. |
| 2015/0254677 A1* | 9/2015 | Huxham ............ G06K 19/0709 705/57 |
| 2016/0267769 A1 | 9/2016 | Rokhsaz et al. |
| 2017/0065464 A1* | 3/2017 | Heil ................... A61F 13/42 |
| 2017/0098044 A1 | 4/2017 | Lai et al. |

FOREIGN PATENT DOCUMENTS

| | | |
|---|---|---|
| CN | 102568259 A | 7/2012 |
| CN | 202711437 U | 1/2013 |
| CN | 102985853 A | 3/2013 |
| DE | 4137631 A1 | 5/1992 |
| DE | 69906388 T2 | 2/2004 |
| DE | 69915370 T2 | 3/2005 |
| DE | 69917491 T2 | 5/2005 |
| DE | 60016946 T2 | 6/2006 |
| DE | 102007050074 A1 | 4/2009 |
| EP | 0335279 A1 | 10/1989 |
| EP | 1286179 A2 | 12/1999 |
| EP | 1147603 A2 | 10/2001 |
| EP | 1149305 A2 | 10/2001 |
| EP | 1153317 A2 | 11/2001 |
| EP | 1218771 A2 | 7/2002 |
| EP | 1153317 B1 | 3/2003 |
| EP | 1147603 B1 | 3/2004 |
| EP | 1410353 A2 | 4/2004 |
| EP | 1149305 B1 | 5/2004 |
| EP | 1218771 B1 | 12/2004 |
| EP | 1286179 B1 | 11/2005 |
| EP | 1684615 A1 | 8/2006 |
| EP | 1868553 A1 | 12/2007 |
| EP | 1897278 A1 | 3/2008 |
| EP | 1959900 A1 | 8/2008 |
| EP | 1994650 A2 | 11/2008 |
| EP | 2014267 A1 | 1/2009 |
| EP | 2019659 A1 | 2/2009 |
| EP | 1410353 B1 | 12/2009 |
| EP | 1897278 B1 | 1/2010 |
| EP | 1684615 B1 | 2/2010 |
| EP | 2156222 A1 | 2/2010 |
| EP | 2313044 A2 | 4/2011 |
| EP | 2444039 A1 | 8/2011 |
| EP | 1959900 B1 | 2/2012 |
| EP | 2452183 A1 | 5/2012 |
| EP | 2496197 A1 | 9/2012 |
| EP | 1994650 B1 | 12/2012 |
| EP | 2542200 A1 | 1/2013 |
| EP | 2579069 A2 | 4/2013 |
| EP | 2582341 A1 | 4/2013 |
| EP | 2542200 B1 | 2/2014 |
| EP | 2729107 A1 | 5/2014 |
| EP | 2738748 A1 | 6/2014 |
| EP | 2739254 A1 | 6/2014 |
| EP | 2156222 B1 | 8/2015 |
| EP | 2496197 B1 | 8/2015 |
| EP | 2019659 B1 | 4/2016 |
| EP | 2582341 | 4/2016 |

(56) References Cited

FOREIGN PATENT DOCUMENTS

| EP | 2739254 | | 11/2016 |
|---|---|---|---|
| GB | 145859 | A | 3/1919 |
| GB | 2145859 | A | 4/1985 |
| GB | 2408204 | A | 11/2003 |
| WO | WO 89/10110 | A1 | 11/1989 |
| WO | WO 94/20002 | A1 | 9/1994 |
| WO | WO 00144091 | A2 | 7/2000 |
| WO | WO 01/25817 | A2 | 4/2001 |
| WO | WO 02/103645 | A2 | 12/2002 |
| WO | WO 2006/108540 | A1 | 10/2006 |
| WO | WO 2007/069968 | A1 | 6/2007 |
| WO | WO 2008/130298 | A1 | 10/2008 |
| WO | WO 2010/001271 | A2 | 1/2010 |
| WO | WO 2010/001271 | A3 | 1/2010 |
| WO | WO 2010/043368 | A1 | 4/2010 |
| WO | WO 2011/107580 | A1 | 9/2011 |
| WO | WO 2012/136157 | A1 | 10/2012 |
| WO | WO 2014/165041 | A2 | 10/2014 |
| WO | 2015137999 | A1 | 9/2015 |

OTHER PUBLICATIONS

Non-Final Office Action for U.S. Appl. No. 15/708,589 dated May 23, 2018 (10 pages).
Amendment for U.S. Appl. No. 15/708,589 dated Aug. 8, 2018 (9 pages).
Notice of Allowance for U.S. Appl. No. 15/708,589 dated Sep. 6, 2018 (10 pages).
Extended European Search Report for European Patent Application No. 19186389.3 dated Oct. 22, 2019 (9 pages).

\* cited by examiner

US 10,653,567 B2

INCONTINENCE DETECTION PAD VALIDATION APPARATUS AND METHOD

The present application is a continuation-in-part of U.S. application Ser. No. 15/596,036, which was filed May 16, 2017, which is a continuation-in-part of International Application No. PCT/US2016/062167, which was filed Nov. 16, 2016, which claims the benefit, under 35 U.S.C. § 119(e), of U.S. Provisional Application No. 62/255,592, which was filed Nov. 16, 2015, and each of which is hereby incorporated by reference herein in its entirety.

BACKGROUND

The present disclosure relates to incontinence detection systems and particularly, to incontinence detection systems that use a pad beneath a person lying in a patient bed. More particularly, the present disclosure relates to incontinence detection systems that are able to communicate wirelessly between the pad and a reader on the patient bed.

Incontinence detection systems that have incontinence detection pads placed beneath a patient on a patient bed are known. For example, U.S. Pat. No. 5,537,095 discloses an incontinence detection pad having electrical circuitry that couples via a wired connection to a controller of a patient bed. Recent efforts have involved the development of wireless communication between the circuitry of the incontinence detection and a reader on a patient bed. The antennae in some such prior systems are individually powered by a reader to energize a passive RFID chip on the incontinence detection pad and to read backscattered data sent from the passive RFID chip back to the reader via the antennae.

In the known wireless incontinence detection pad systems, signal to interfere (S/I) ratio issues are prevalent. For example, when a monostatic architecture using a hybrid directional coupler to provide receiver isolation from the transmitter and to allow simultaneous transmission and reception on the same antenna, the coupling between the transmitter and receiver ports of the hybrid coupler is about −10 decibels (dB). This means that 90% of the received signal does not end up in the receiver. Furthermore, if the antenna impedance deviates from the transmission line characteristic impedance, the power reflected from the antenna is coupled into the receiver input and is much stronger than the backscattered signal from the RFID tag, which creates the situation where the receiver must reject a very strong signal near the signal of interest in order to detect and demodulate only the signal of interest, which in the case of an EPC 2 compliant tag, is 256 kilohertz (kHz) away from the carrier. In such situations the S/I ratio can be on the order of 50 dB. An alternative known architecture is the use of a circulator which couples the transmitter and receiver, functionally, in a similar way as a hybrid coupler. However, the S/I ratio using a circulator is only about 1.6 dB better than the hybrid coupler approach.

Other interfering signals include forward power coupling into the receiver port, which can be 5 dB higher than the tag backscattered signal, and power reflected from the RF forward power, which can be 34 dB stronger than the backscattered signal. All of these signals add into the front end of the receiver, which subjects it to overload and intermodulation distortion products which may further impact the performance of the receiver. In other words, because there is a strong signal close in frequency to a weak signal, it is difficult to detect the weak signal. A further concern is that RFID systems that are located in close proximity to a patient's body experience communication channel degradation due to the interaction of the biological tissue and body fluids with the RFID tag.

Based on the foregoing, it should be apparent that there is an ongoing need for improved electrical architecture in wireless incontinence detection pad systems used on patient support apparatuses such as patient beds.

SUMMARY

The present application discloses one or more of the features recited in the appended claims and/or the following features which, alone or in any combination, may comprise patentable subject matter:

According to the present disclosure, an incontinence detection system may include an incontinence detection pad for placement beneath a person to be monitored. The incontinence detection pad may have a passive radio frequency identification (RFID) tag. A reader may be provided and a plurality of antennae may be coupled to the reader. The reader may include a bistatic radio frequency (RF) switch matrix which may be operable to establish a first antenna of the plurality of antennae as a transmit antenna that may be used to wirelessly energize the passive RFID tag and to establish a second antennae of the plurality of antennae as a receive antenna that may be used to read backscattered data that may be emitted from the passive RFID tag. The first and second antennae may be situated in respective housings that are spaced apart from each other.

In some embodiments, the plurality of antennae may include a third antenna and a fourth antenna. The bistatic RF switch matrix may be operated in a full cycle scanning mode so that each of the first, second, third and fourth antenna may be selectively chosen to be established as the transmit antenna and each of the remaining antenna may be selectively cycled through to be the receive antenna such that twelve transmit antenna and receive antenna combinations may be operated.

During the full cycle mode, the transmit antenna and receive antenna combinations that may produce valid reads of the RFID tag may be stored. A modified cycle scanning mode then may be determined for operation of the bistatic RF switch matrix based on the valid reads such that only transmit antenna and receive antenna combinations that produced valid reads may be cycled through for a predetermined number of cycles, after which the bistatic RF switch matrix may be once again operated in the full cycle scanning mode. If no valid reads of the passive RFID tag are detected during the full cycle scanning mode, then the bistatic RF switch matrix may continue to operate in the full cycle scanning mode until at least one valid read is detected, after which the bistatic RF switch matrix may be operated in the modified cycle scanning mode.

In some embodiments, the plurality of antennae may be operated by the reader by transmitting using a frequency hopping scheme at a power less than or equal to 1 Watt (W). The frequency hopping scheme may use 50 distinct frequencies, for example, with each frequency being used only once in a pseudo-random order before any of the 50 frequencies may be repeated. Optionally, the 50 frequencies may lie within a range between about 902 MegaHertz (MHz) and 928 MHz. At least one antenna of the plurality of antennae may comprise a ½ wave ceramic patch antenna. If desired, however, each antenna of the plurality of antennae may comprise a ½ wave ceramic patch antenna.

The incontinence detection system may further include a patient bed that may have a frame and a mattress support deck that may be carried by the frame. The mattress support deck may include a head section, a seat section, and a thigh section. At least the head section and the thigh section may be raiseable and lowerable relative to the frame. The first and second antennae may be coupled to the head section, the third antenna may be coupled to the seat section, and the fourth antenna may be coupled to the thigh section. Alternatively, the first antenna may be coupled to the head section, the second and third antennae may be coupled to the seat section, and the fourth antenna may be coupled to the thigh section. Further alternatively, the first antenna may be coupled to the head section, the second antenna may be coupled to the seat section, and the third and fourth antennae may be coupled to the thigh section.

In some embodiments, the incontinence detection may further include a patient bed that may have a frame and a mattress support deck carried by the frame. The mattress support deck may include a first section and a second section that each may be raiseable and lowerable relative to the frame. The first section and the second section each may be formed in a step deck arrangement that may have a bottom wall and a side wall that may extend generally upwardly from the bottom wall. The first antennae may be coupled to the bottom wall of the first section, the second antenna may be coupled to a side wall of the first section, the third antenna may be coupled to the bottom wall of the second section, and the fourth antenna may be coupled to the side wall of the second section.

It is within the scope of this disclosure that the incontinence detection system may further include a patient bed that may have a frame and a mattress support deck carried by the frame. The reader may be coupled to the frame and the plurality of antennae may be coupled to the mattress support deck so as to be closer to a first side of the mattress support deck than an opposite second side of the mattress support deck.

In some embodiments, the incontinence detection system may further include an indicator that may be located adjacent a foot end of the bed and that may be operable to indicate that an incontinence event has occurred. Optionally, an output port may be located adjacent a head end of the bed and may be connectable to a nurse call system for providing incontinence event data to the nurse call system.

According to the present disclosure, an electrical sheet for an incontinence detection pad may be provided. The electrical sheet may include a layer of material that may be shaped generally as a rectangle that may have first and second long sides and first and second short sides. An RFID tag may be coupled to the layer closer to the first short side than the second short side. First and second electrodes may be provided on the layer and may be electrically coupled to the RFID tag. The first and second electrodes may include first, second, third and fourth electrode segments that may be generally parallel with the first and second long sides of the layer. The second and third electrode segments may be situated between the first and fourth electrode segments. The second and third electrode segments may be spaced apart by a first distance that may be at least twice a second distance that may be defined between the first and second electrode segments and between the third and fourth electrode segments.

The first and second electrodes may also provide fifth, sixth, seventh and eighth electrode segments that may be generally parallel with the first and second short sides of the layer. The sixth and seventh electrode segments may be situated between the fifth and eighth electrode segments. The fifth and sixth electrode segments may be spaced apart by a third distance that may be at least six times a fourth distance that may be defined between the fifth and sixth electrode segments and between the seventh and eighth electrode segments.

The fifth and seventh electrode segments may be included as part of the first electrode and the sixth and eighth electrode segments may be included as part of the second electrode. The first and third electrode segments may be included as part of the first electrode and wherein the second and fourth electrode segments may be included as part of the second electrode. The layer may be devoid of any electrode portions between the second and third electrode segments.

In some embodiments, the first distance between the second and third electrode segments may be greater than 30% of a third distance that may be defined between the first and second long sides of the layer. For example, the first distance between the second and third electrode segments may be greater than 40% of a third distance that may be defined between the first and second long sides of the layer. The spacing between the second and third electrode segments is intended to be sufficiently large to prevent a gel or ointment applied to a patient's buttocks and/or sacral region from providing an electrically conductive path between the second and third electrode segments that are oriented parallel with the first and second long sides of the layer.

According to a further aspect of this disclosure, an electrical sheet for an incontinence detection pad is provided. The electrical sheet may include a layer of material shaped generally as a rectangle having first and second long sides and first and second short sides. An RFID tag may be coupled to the layer closer to the first short side than the second short side. First and second electrodes may be provided on the layer and may be electrically coupled to the RFID tag. The first and second electrodes may include first, second, third and fourth electrode segments that may be generally parallel with the first and second short sides of the layer. The second and third electrode segments may be situated between the first and fourth electrode segments. The second and third electrode segments may be spaced apart by a first distance that may be at least six times a second distance that may be defined between the first and second electrode segments and between the third and fourth electrode segments.

The layer may be devoid of any electrode portions between the second and third electrode segments. The first distance between the second and third electrode segments may be greater than 50% of a third distance defined between the first and second short sides of the layer. The spacing between the second and third electrode segments is intended to be sufficiently large to prevent a gel or ointment applied to a patient's buttocks and/or sacral region from providing an electrically conductive path between the second and third electrode segments that are oriented parallel with the first and second short sides of the layer.

In some embodiments, the electrical sheet may further have at least one icon that may include a water droplet with WiFi curves and that may be printed on a surface of the layer that may be opposite from a surface on which the first and second electrodes may be provided. Optionally, the layer may include a first substrate that may be made of a fluid impermeable material and a second substrate that may be made of a nonwoven material. The first and second electrodes may be located on the fluid impermeable material and the at least one icon may be located on the nonwoven material.

For each of the above aspects and embodiments contemplated herein, a reader of an incontinence detection system may be equipped with an 802.11 wireless communication capability for communication with a wireless access point which may, in turn, be connected via a network to a remote computer, such as a remote computer or server of a Clinical Workflow Solutions (CWS) medical data management system. The CWS system may or may not be included as part of nurse call system, for example. The reader may send tag identification (ID) and an encrypted ID, both of which may be received by the reader from a RFID tag of an incontinence detection pad, to the remote server of the CWS system for remote validation of the incontinence detection pad that may be placed on a bed. More than one pad may be placed on the bed 10 in which case the reader may receive more than one tag ID and more than one encrypted ID. The CWS system may perform decryption remotely and may compare the tag ID and the data that may be derived from decrypting the encrypted ID from the tag to complete the validation. If desired, the data sent from the reader may be protected against transmission errors corrupting the data with standard Internet Protocol error checking algorithms and/or additional error detection that may be applied by the reader at the bed.

By moving the validation operation to a remote site, such as a computer or server of CWS system that may have internet connectivity may result in a number of advantages. Firstly, the processor of the reader at the bed may not have the computational resources either in terms of memory or CPU cycles to accomplish the decryption locally. Secondly, the encryption algorithm may be changed at will and the algorithm that may be used may be determined by the tag ID so the deployment in the field may be seamless. The encryption details and private keys may be managed by an online connection to a secure server at another facility (e.g., a server at the entity which may manufacture or sell the incontinence detection system and/or the bed), which may enable the modification of the private key on an as-needed basis, a periodic change in private key or the wholesale replacement of the encryption algorithm in a secure fashion. In this way, the data generated for pad validation may be done in an entirely secure fashion, and may be done on an as needed basis. If it is detected that the private key has become compromised, a new private key may be instituted and the pad serial numbers/private key may be maintained in a database at the CWS server for pad validation.

In some embodiments, the incontinence detection systems and the bed may be used in home healthcare and other markets outside a traditional hospital or other healthcare facility. For such markets, the reader may be constructed with a very limited functionality microprocessor by having the high compute resource intensity operations, such as decryption algorithms, accomplished remotely via any available internet connection. As a collateral benefit, a service may be used to automatically bill and send more incontinence pads to a customer (via prior arrangement), thereby enabling e-commerce business using existing hardware connections. Thus, a server of the CWS system or a server at a remote facility may perform pad usage data collection, may perform billing functions, and/or may generate inventory management data, as well as provide other notifications to hospitals or home users about incontinence detection pad usage. For example, such usage data may include a number of pads used per day, week, and/or month; average amount of time before a dry pad becomes soiled; average amount of time after soiling before the wet pad is removed and/or replaced with a dry pad; and number of pads remaining from prior shipment quantity for usage.

Additional features, which alone or in combination with any other feature(s), including those listed above and those listed in the claims, may comprise patentable subject matter and will become apparent to those skilled in the art upon consideration of the following detailed description of illustrative embodiments exemplifying the best mode of carrying out the invention as presently perceived.

BRIEF DESCRIPTION OF THE DRAWINGS

The detailed description particularly refers to the accompanying figures in which.

DETAILED DESCRIPTION

Referring now to FIGS. 1-7, an incontinence detection system 20 is attached to different types of hospital beds 10.

Figure 1:
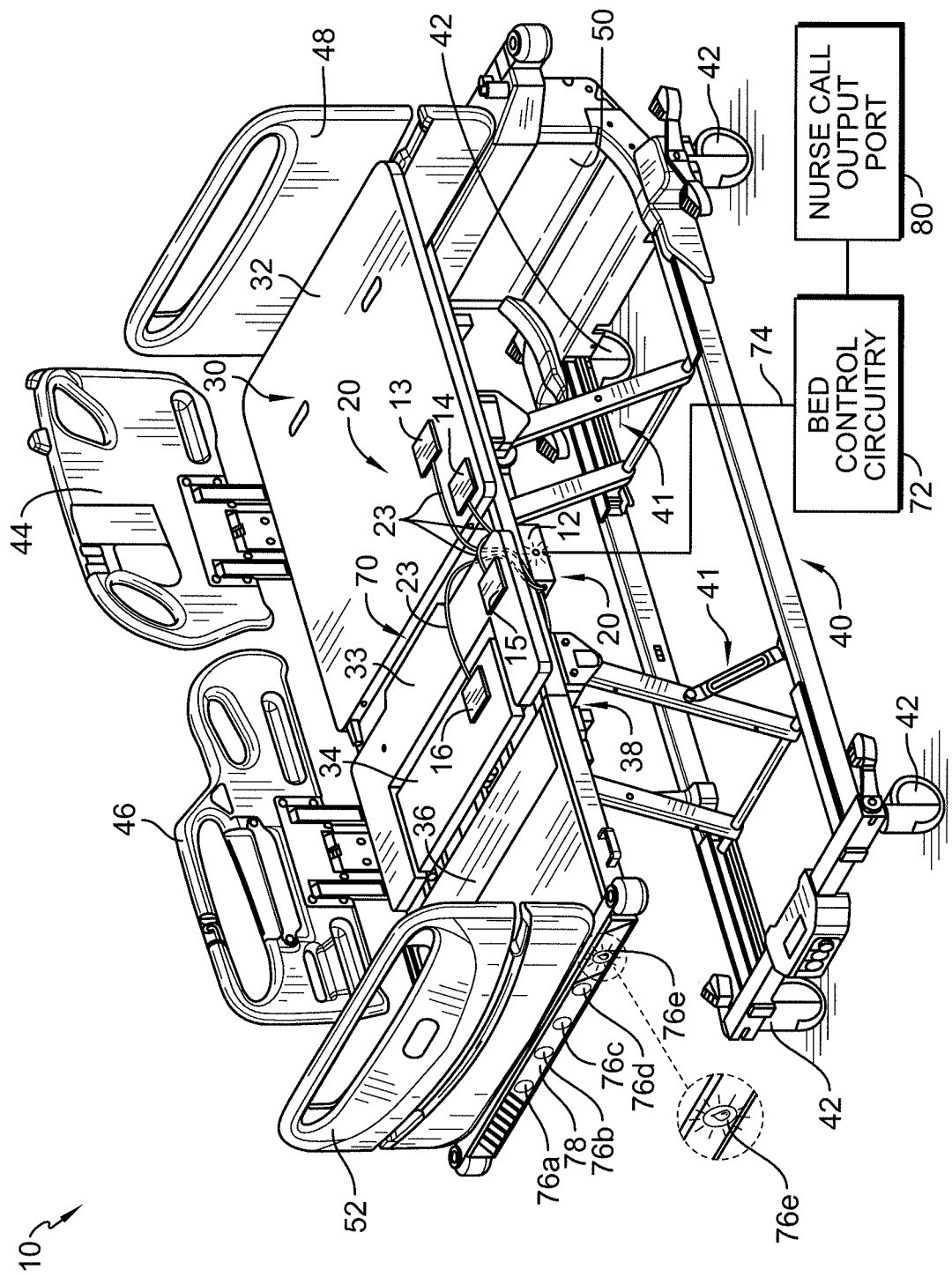
FIG. 1 is a perspective view showing four antenna, a reader, and a visual indicator of an incontinence detection system installed on a first embodiment of a patient bed with first and second antennae being coupled to a head section of the patient bed, a third antenna coupled to a seat section of the patient bed, and a fourth antenna coupled to a thigh section of the patient bed and showing, diagrammatically, the reader being coupled electrically to bed control circuitry to send incontinence detection data via the bed control circuitry to a nurse call output port of the patient bed.
Figure 2:
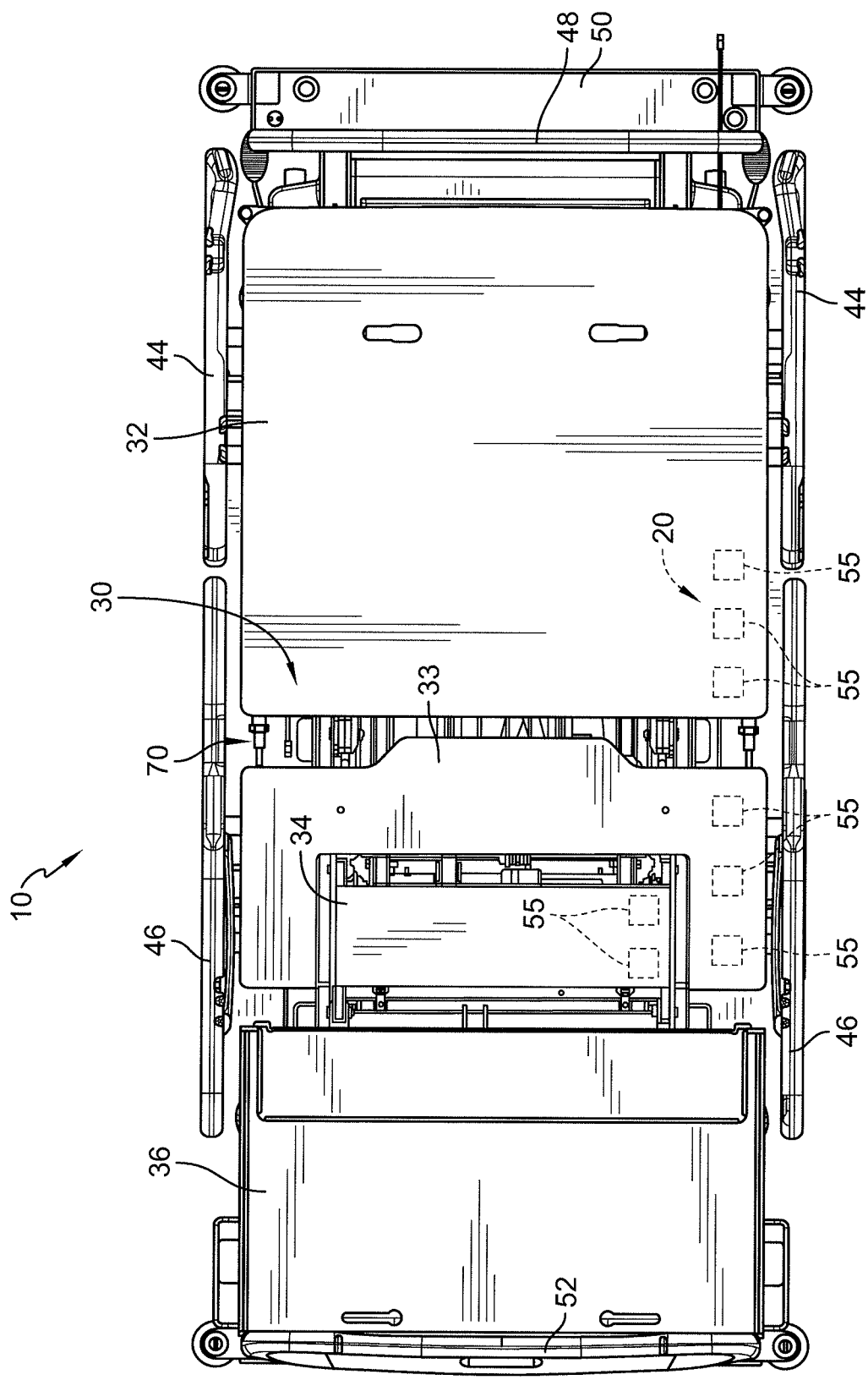
FIG. 2 is a top plan view of the patient bed of FIG. 1 showing dotted boxes indicating some, but not all, possible locations on the head, seat and thigh sections for placement of the four antennae of the incontinence detection system.
Figure 3:
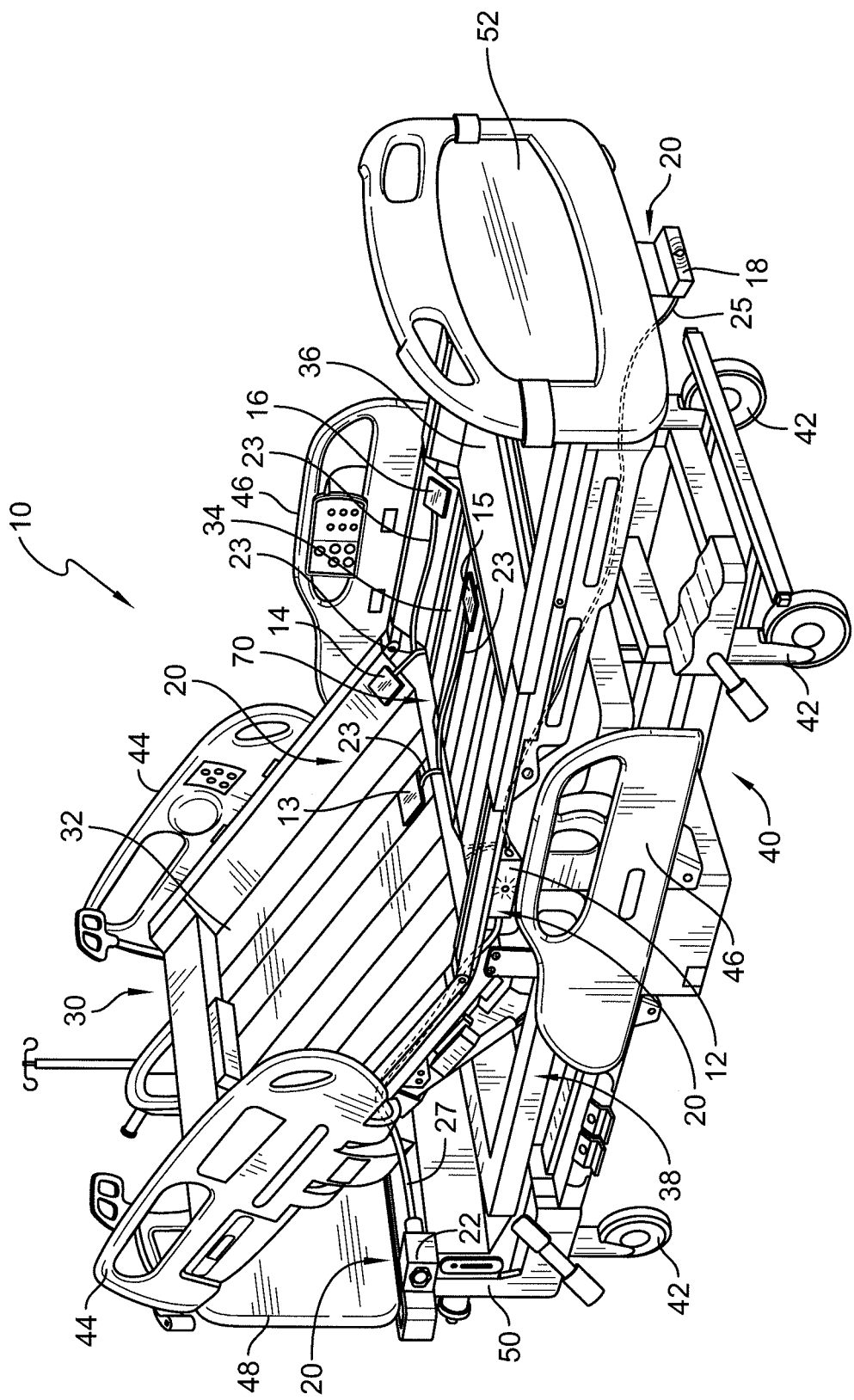
FIG. 3 is a perspective view, similar to FIG. 1, showing the four antennae, the reader, a visual indicator, and an output port of another embodiment of an incontinence detection system retrofitted on a second embodiment of a patient bed with the first and second antennae being coupled to a head section of the patient bed and the third and fourth antenna being coupled to a thigh section of the patient bed.
Figure 4:
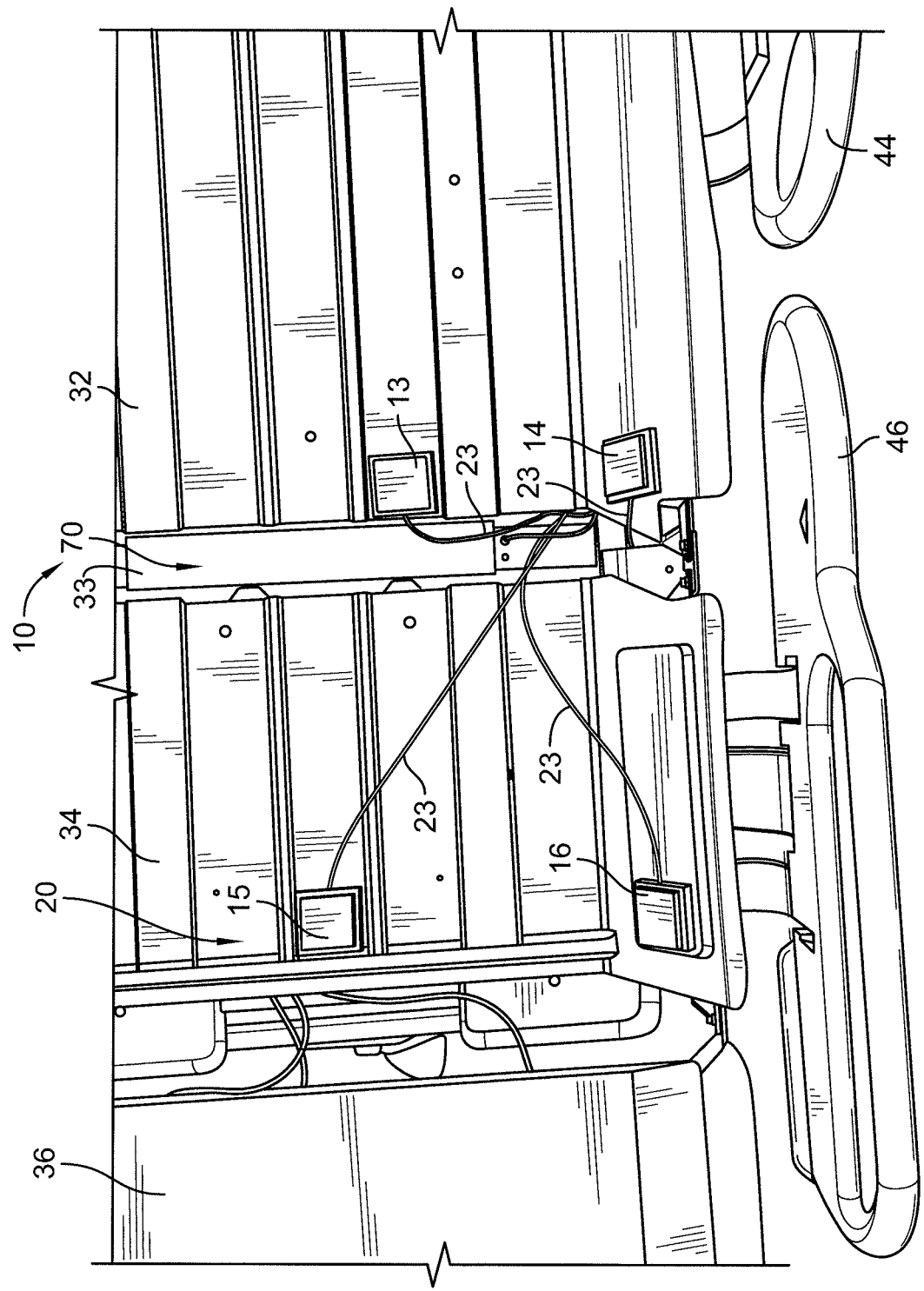
FIG. 4 is a top plan view of a portion of the patient bed of FIG. 3 showing the four antennae on the head and thigh sections of the patient bed.
Figure 5:
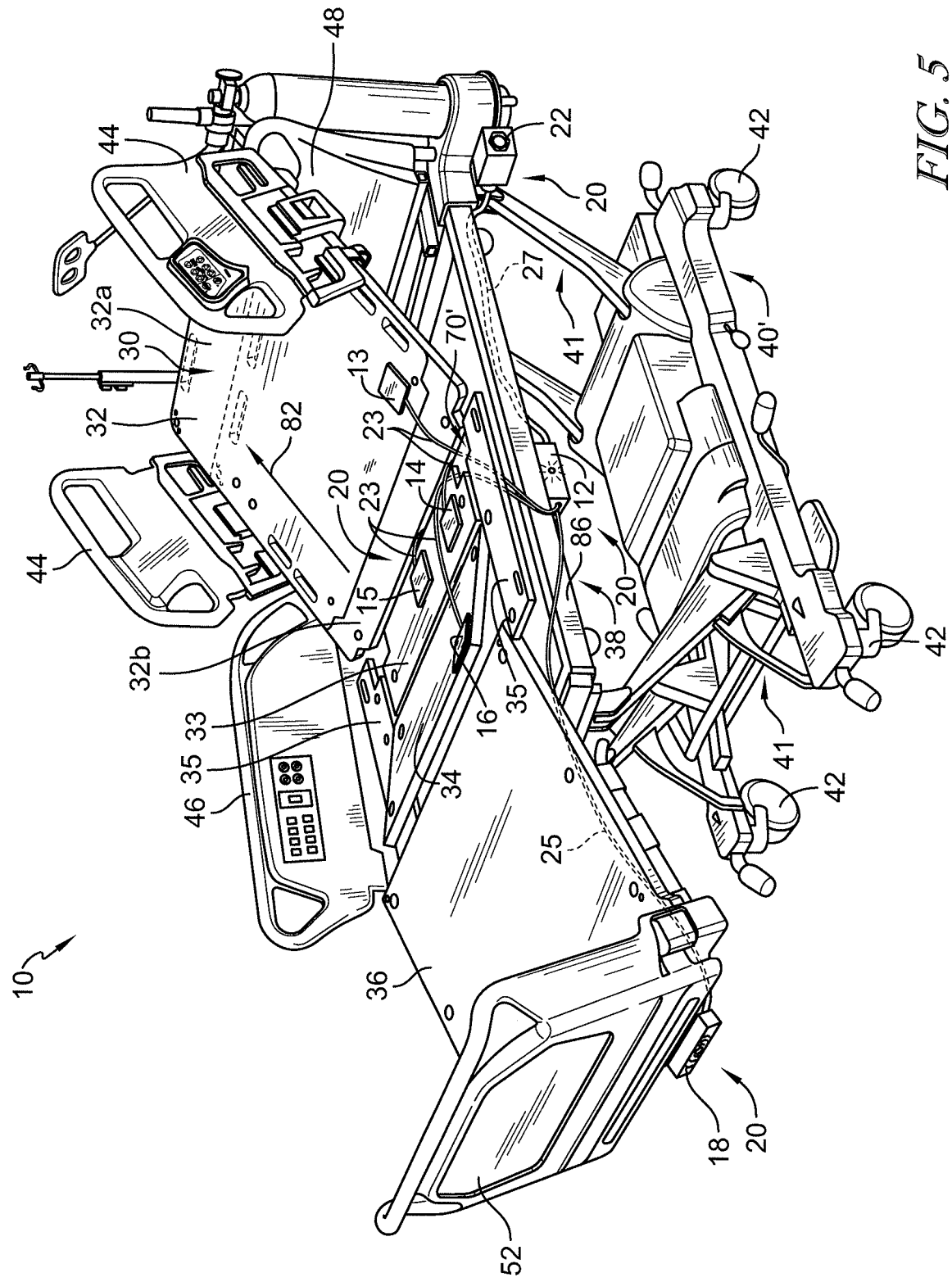
FIG. 5 is a perspective view, similar to FIG. 1, showing the four antenna, the reader, the visual indicator, and the output port of the incontinence detection system retrofitted on a third embodiment of a patient bed with the first antenna being coupled to a slideable panel of a head section of the patient bed, the second and third antenna coupled to a seat section of the patient bed, and the fourth antenna coupled to a thigh section of the patient bed.
Figure 6:
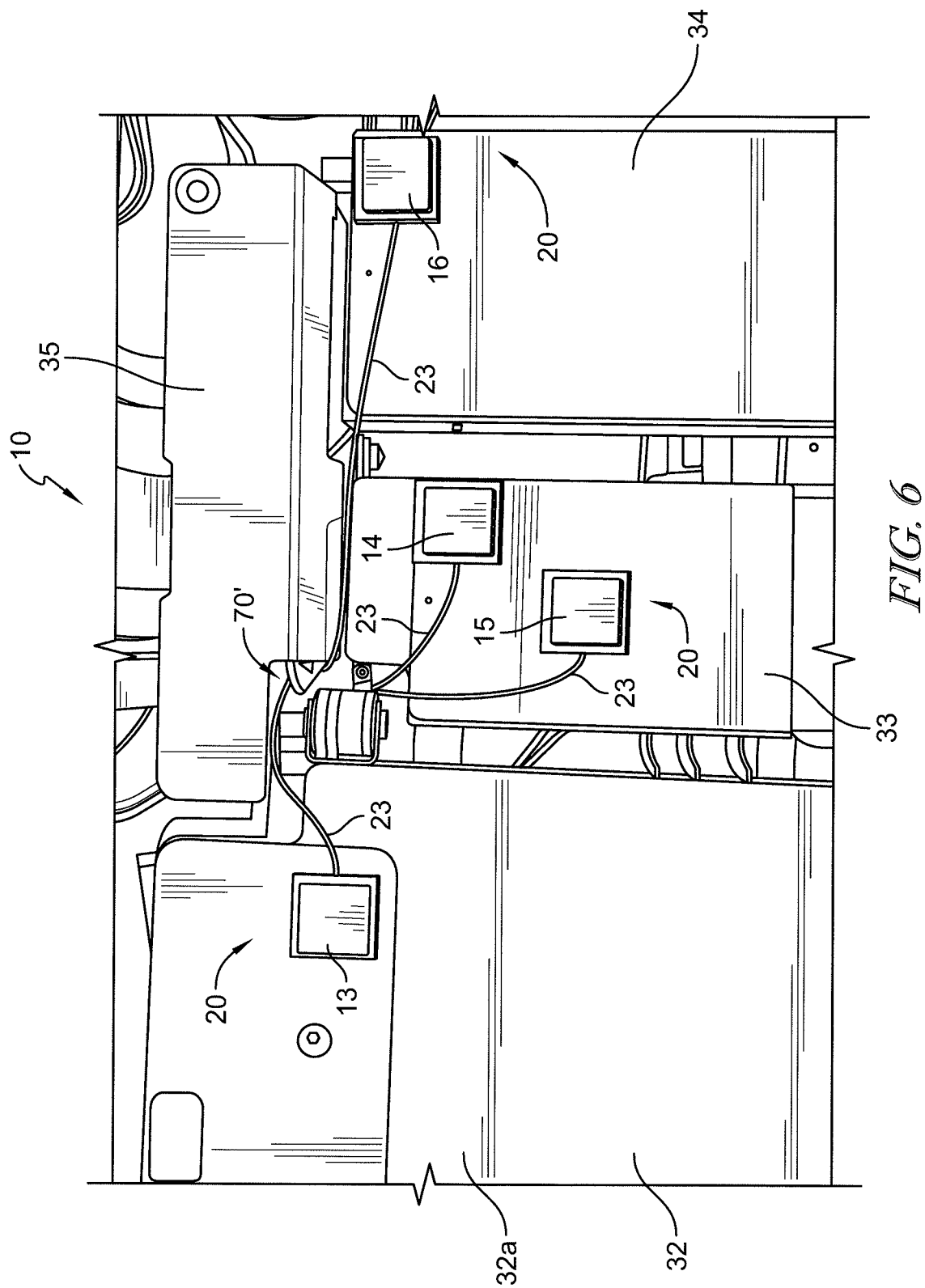
FIG. 6 is a top plan view of a portion of the patient bed of FIG. 5 showing the four antennae on the head, seat and thigh sections of the patient bed.

The bed 10 of FIGS. 1 and 2 is marketed as the CENTRELLA™ Smart+Bed by Hill-Rom Company, Inc. Further details of bed 10 of FIGS. 1 and 2 can be found in International Patent Application No. PCT/US2016/034908, which was filed May 29, 2016, and which is hereby incorporated by reference herein in its entirety. The bed 10 of FIGS. 3 and 4 is illustrative of the VERSACARE® bed available from Hill-Rom Company, Inc. The bed 10 of FIGS. 5 and 6 is illustrative of the PROGRESSA® bed available from Hill-Rom Company, Inc. The bed 10 of FIG. 7 is a generic bed which is shown diagrammatically.

Figure 7:
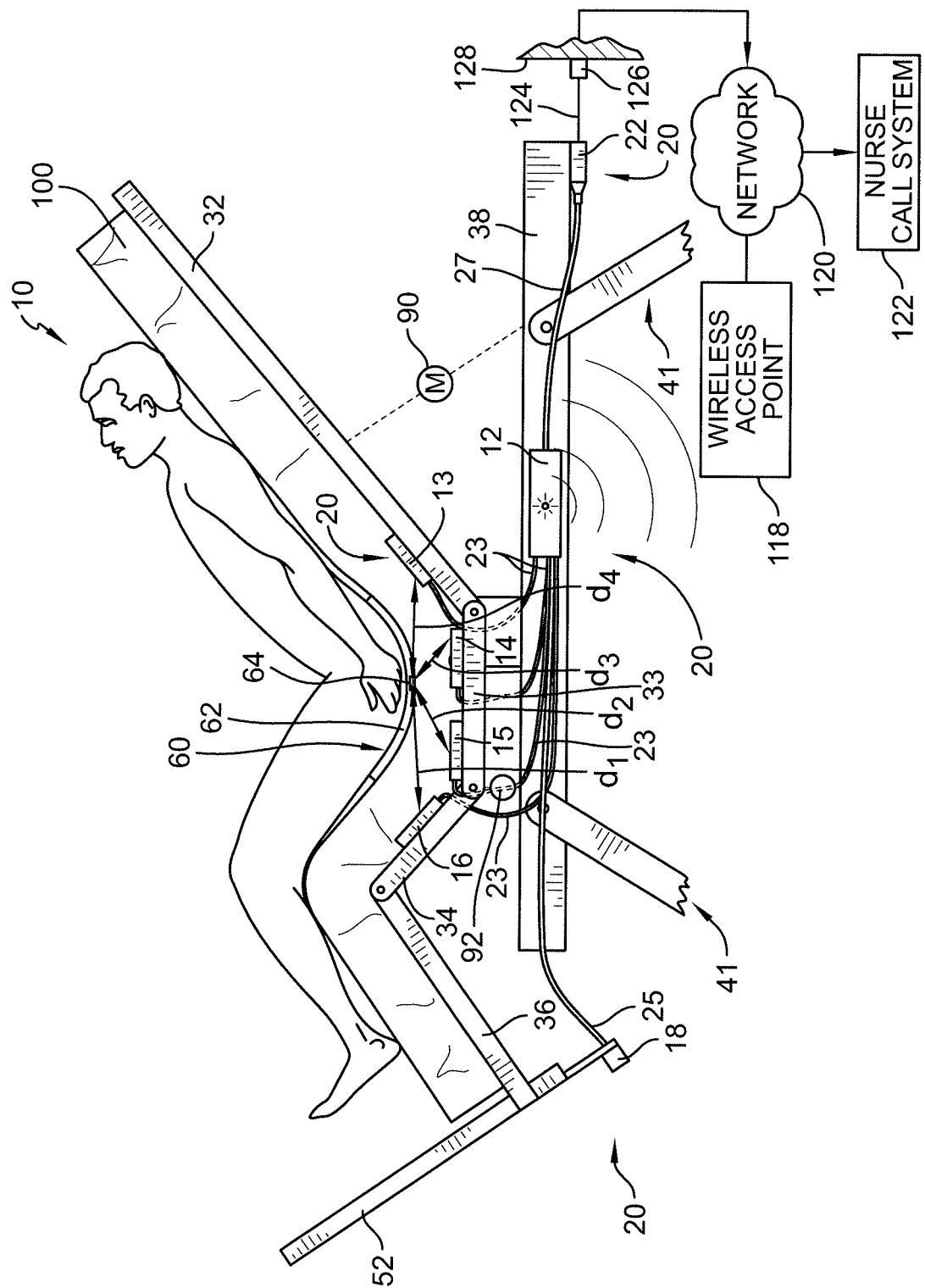
FIG. 7 is a diagrammatic view showing distances between each of the four antennae of the incontinence detection system and an RFID tag of an incontinence detection pad situated between a patient and an upper surface of a mattress of a patient bed and showing the reader communicating with a network via wired and wireless datalinks.

With the exception of bed 10 of FIGS. 1 and 2, which will be discussed below, the incontinence detection system 20 includes a reader 12; first, second, third and fourth antennae 13, 14, 15, 16; a visual indicator 18; and an output port 22 as shown in FIGS. 3, 5 and 7. A respective cable 23 electrically couples each antenna 13, 14, 15, 16 to reader 12. A cable 25 electrically couples reader 12 to visual indicator 18 and a cable 27 electrically couples reader 12 to output port 22. Incontinence detection system 20 also includes one or more incontinence detection pads 60 on bed 10. Pads 60 have a moisture absorbing substrate 62 and a passive RFID tag 64 within the substrate 60 as shown diagrammatically in FIG. 7. At least two electrode traces are coupled to the passive RFID tag and extend therefrom within the substrate as will be discussed below in connection with FIG. 9.

Reader 12 is operated so that a selected one of antennae 13, 14, 15, 16 is established as a transmit antenna and another of antennae 13, 14, 15, 16 is established as a receive antenna. As will be described in further detail below, reader 12 is operated to cycle through each antenna 13, 14, 15, 16 as being the transmit antenna and to cycle through the remaining three antennae, one at a time, as being the receive antenna. The transmit antenna emits wireless energy to power an RFID chip of RFID tag 64 and, in response, the RFID tag transmits backscattered data which is potentially read by the receive antenna. The data indicates whether the pad 60 is wet or dry. The pad 60 is considered "wet" if there is enough moisture or liquid, such as incontinence, to bridge a space between the electrode traces and the pad 60 is considered "dry" if there is insufficient moisture or liquid to bridge the space between the electrode traces.

Bed 10 of FIGS. 1 and 2 has a mattress support deck 30 with a head section 32, a seat section 33, a thigh section 34, and an extendable and retractable foot section 36. In the illustrative example, seat section 33 is U-shaped and thigh section 34 nests within the cavity formed by the U-shape of seat section 33. In FIGS. 1 and 2, sections 32, 33, 34, 36 are oriented generally horizontally such that the upper surfaces of sections 32, 33, 34, 36 are generally coplanar with each other. Bed 10 of FIGS. 1 and 2 has an upper frame 38 upon which sections 32, 34, 36 of deck 30 are supported for pivoting or articulating movement. Seat section 33 is stationary relative to upper frame 38 in bed 10 of FIGS. 1 and 2.

Bed 10 of FIGS. 1 and 2 also has a base frame 40 which is supported on a floor by a set of four casters 42. Bed 10 has a lift system to raise, lower and tilt upper frame 38 relative to base frame 40 as is known in the art. The lift system is in the form of linkages 41 and motorized linear actuators in some embodiments. Bed 10 of FIGS. 1 and 2 has a pair of head end siderails (sometimes referred to as head rails) 44 that are mounted to and move with head section 32 as it is pivotably raised and lowered relative to upper frame 38, a pair of foot end siderails 46 (sometimes referred to as foot rails) that are mounted to upper frame 38, a headboard 48 removably coupled to an upstanding portion 50 of base frame 40, and a footboard 52 removably coupled to a foot end portion of foot section 36 which is the extendable and retractable portion of foot section 36. In FIG. 1, the head rail 44 and the foot rail 46 at the left side of bed 10 have been removed so that reader 12 and antennae 13, 14, 15, 16 can be seen.

In the illustrative FIGS. 1 and 2 example of bed 10, antennae 13, 14 are coupled to head section 32 near the left edge thereof and more toward the foot end of head section 32. Antenna 14 is coupled to seat section 33 near the left edge therefor and more toward the head end of seat section 33. Antenna 16 is coupled to thigh section 34 near the left edge thereof and more toward the head end of thigh section 34. The placement of antennae 13, 14, 15, 16 on sections 32, 33, 34 is a matter of trial and error based on the locations that produce the best results for reading tags 64 of incontinence detection pads 60 that are used on bed 10. Thus, in FIG. 2, a number of dotted boxes 55 are shown to indicate a sampling of some, but not all, possible locations on sections 32, 33, 34 at which antennae 13, 14, 15, 16 may be placed. In the illustrative example, antennae 13, 14, 15, 16 are closer to the left side of bed 10 because incontinence detection pad has RFID tag 64 nears its left side. In other embodiments, antennae 13, 14, 15, 16 are coupled to deck 30 closer to the right side thereof.

In the illustrative FIGS. 1 and 2 example, cables 23 are routed from respective antennae 13, 14, 15, 16 to reader 12 through a space or gap 70 formed between a foot end of head section 32 and a head end of seat section 33. One key difference between the incontinence detection system 20 of FIGS. 1 and 2 and those of FIGS. 3-7 is that visual indicator 18, output port 20, and cables 25, 27 are omitted in the FIGS. 1 and 2 system 20. Instead, reader 12 is electrically coupled to bed control circuitry 72 via a suitable cable 74 as shown diagrammatically in FIG. 1.

Bed 10 of FIGS. 1 and 2 has a series of alert lights 76a, 76b, 176c, 76d, 76e that are included in a foot end frame member 78 of foot section 36 and that are controlled by bed control circuitry 72. Alert lights 76a-e are similar to those shown and described in International Patent Application No. PCT/US2016/034908 which is already incorporated by reference herein (see particularly, FIG. 97 along with the related discussion of that document). For purposes of this disclosure, alert light 76e is the one that is illuminated in connection with the incontinence detection system 20 of bed 10 of FIGS. 1 and 2. Circuitry 72 of bed 10 commands alert light 76e to shine or illuminate white light when reader 12 is turned on but no incontinence detection pad 60 is detected. Circuitry 72 of bed 10 commands alert light 76e to shine green light when reader 12 is turned on and is communicating with an incontinence detection pad 60 that is dry, or at least not sufficiently wet to be sensed by the pad 60. Circuitry 72 of bed 10 commands alert light 76e to shine yellow (aka amber) light, and to flash in some embodiment, when reader 12 is turned on and is communicating with an incontinence detection pad 60 that is wet.

Bed circuitry 72 is operable to output bed data, including data detected by the incontinence detection system 20, through a nurse call output port 80 shown diagrammatically in FIG. 1. Port 80 is a 37-pin connector in some embodiments, for example. Such 37-pin connectors are known connectors which are sometimes used on hospital beds for communication with a nurse call system of a healthcare facility. In some embodiments, the incontinence detection information or data, such as data including information regarding whether the incontinence detection pad 60 has detected wetness, is transmitted from bed 10 by circuitry 72 via port 80 in one or more data packets that also include the other bed data. In other embodiments, the incontinence detection information is transmitted in one or more data packets that do not include the bed data. That is, the incontinence detection data can be transmitted in the same data packets as the bed data or in separate packets.

Each antenna 13, 14, 15, 16 is smaller than the two antennae disclosed in International Patent Application No. PCT/US2016/062167, filed Nov. 16, 2016, titled "Incontinence Detection Systems for Hospital Beds," and owned by the same Assignee as the present application. A footprint of each antenna 13, 14, 15, 16 is about three inches by three inches. Furthermore, each antenna 13, 14, 15, 16 comprises a ½ wave ceramic patch antenna. This type of antenna is an improvement over the antenna disclosed in International Patent Application No. PCT/US2016/062167. In particular, about 25 to about 30 dB of isolation is achieved by using the ½ wave ceramic patch antenna as part of antennae 13, 14, 15, 16 which represents better isolation by about 15 to about 25 dB as compared to a directional coupler design. This is because the reflected power signal back from the transmit antenna is no longer coupled into the receiver of reader 12. The receiver circuitry of reader 12 is isolated from the transmitter circuitry.

Referring now to FIGS. 3 and 4, the illustrative bed 10 is similar to that of FIGS. 1 and 2 such that like reference numbers are used to denote like components of these beds. The description above of bed 10 of FIGS. 1 and 2 is equally applicable to bed 10 of FIGS. 3 and 4 except where noted in the description that follows. Bed 10 of FIGS. 3 and 4 has a mattress support deck 30 with a dished head section 32, a dished thigh section 34, and an extendable and retractable foot section 36. A seat section 33 in the form of a smaller dished panel is situated in the space between head section 32 and thigh section 34 as shown in FIG. 4. Bed 10 of FIGS. 3 and 4 has upper frame 38 upon which sections 32, 34, 36 of deck 30 are supported for pivoting or articulating movement. Seat section 33 is stationary relative to upper frame 38 in bed 10 of FIGS. 3 and 4. Deck 30 of FIGS. 3 and 4 is sometimes referred to as a step deck in the art due to the dished shape of some or all of the deck sections 32, 33, 34, 36. Additional details of the VERSACARE® bed 10 shown in FIGS. 3 and 4 can be found in *Service Manual, VersaCare® Bed, from Hill-Rom, Product P3200/P3201,* © 2008 by Hill-Rom Services, Inc. and in U.S. Pat. No. 7,533,429, each of which is hereby incorporated by reference herein for all that it teaches.

As shown in FIG. 3, reader 12 is shown mounted to an underside of a frame member of thigh section 34. Thus, in the illustrative example, reader 12 articulates with thigh section 34 as thigh section 34 pivots relative to upper frame 38. In other embodiments, reader 12 is mounted to upper frame 38. Reader 12 may become blocked from view in the illustrative example when the adjacent siderail 46 is moved from the illustrative lowered position up to a raised position. It should be appreciated that each of siderails 44, 46 is movable between raised and lowered positions relative to their respective support structure (e.g., head section 32 in the case of siderails 44 and upper frame 38 in the case of siderails 46).

Antennae 13, 14 of FIGS. 3 and 4 are mounted to head section 32 closer to the left side of bed 10 than to the right side. In particular, antenna 13 is mounted to a bottom panel of deck section 32 and antenna 14 is mounted to an angled sidewall of deck section 32. Both antennae 13, 14 are situated adjacent to a foot end of deck section 32. Similarly, antennae 15, 16 are mounted to thigh section 34 closer to the left side of bed 10 of FIGS. 3 and 4 than to the right side. In particular, antenna 15 is mounted to a bottom panel of deck section 34 and antenna 16 is mounted to an angled sidewall of deck section 34. Both antennae 15, 16 are situated adjacent to a foot end of deck section 34 in the illustrative example. The left and right sides of bed 10 correspond to left and right sides of a patient lying in bed 10 in a supine position. In some embodiments, strips of hook and loop fasteners (not shown) are used to hold antennae 1114, 1116 in place on the respective deck sections 32, 34.

The reason for locating antennae 13, 14, 15, 16 closer to the left side of bed 10 is twofold. First, the thickness of each antenna 13, 14, 15, 16 is in the range of about ½ inch, give or take a ¼ inch or so, and therefore, by placing the antennae 13, 14, 15, 16 closer to the left side of deck 30, a patient positioned on a mattress supported by deck 30 is less likely to "feel" the antennae 13, 14, 15, 16 through the mattress. Second, incontinence detection pads 60 contemplated by this disclosure have RFID tags 64 situated near the left side of the pads 60. Thus, the antennae 13, 14, 15, 16 which emit or radiate energy to power the RFID tags 64 and to read the data sent or reflected back from the RFID tags 64 operate more efficiently when they are closer to the RFID tags 64. Accordingly, it should be appreciated that, in alternative embodiments of incontinence detection system 20, antennae 13, 14, 15, 16 may be located closer to the right side of bed 10 if the incontinence pads 60 of such alternative embodiments have their respective RFID tags 64 situated near the right sides of the pads 60 rather than the left sides. Alternatively or additionally, deck sections 32, 34 may be formed with recesses in which respective antennae 13, 14, 15, 16 are received so that upper surfaces of antennae 13, 14, 15, 16 are generally flush with upper surfaces of the bottom panel of deck sections 32, 34.

In the embodiment of FIGS. 3 and 4, cables 23 are routed from respective antennae 13, 14, 15, 16 to reader 12 through a gap or space 70 defined between a foot end of head section 32 and a head end of thigh section 34. In the illustrative FIGS. 3 and 4 example, all four cables 23 are routed through a space between a head end of the seat section 33 and the foot end of the head section 32. However, some or all of cables 23 may just as well be routed through a space between a head end of the thigh section 34 and a foot end of the seat section 33. Regardless of the exact routing path, cables 23 are provided with sufficient slack to permit head section 32 and thigh section 34 to pivot through their full ranges of movement relative to upper frame 38.

Cable 25 is routed from reader 12 to visual indicator 1118 along an underside of thigh section 34 and foot section 36 as shown in FIG. 3. Because visual indicator 18 is mounted to the portion of foot section 36 that extends and retracts, cable 25 is provided with sufficient slack to permit the extension and retraction of foot section 36 through its full range of movement. Cable 27 is routed from reader 12 to output port 22 along portions of deck 30 and frames 38, 40 as desired. Because output port 22 is mounted to upstanding portion 50 of base frame 40 and because reader 12 is mounted to deck 30 or frame 38, as the case may be, which are able to be raised, lowered and tilted relative to base frame 40, cable 27 is provided with sufficient slack to permit the upper frame 38, along with deck 30, to be raised, lowered and tilted relative to base frame 40 through its full range of movement.

Suitable cable management devices such as zip ties, hooks, clips, straps, bands, and the like are provided in some embodiments to attach cables 23, 25, 27 to portions of bed 10 at various locations to prevent unwanted sagging or movement of cables 23, 25, 27. However, as suggested above, some portions of cables 23, 25, 27 should be sufficiently slack to permit movement of the various portions of bed 10 without stretching, pinching or binding the respective cable 23, 25, 27. Reader 12 of FIGS. 3 and 4 commands indicator 18 to shine white, green, or amber light to indicate the same information as discussed above in connection with indicator 76e of bed 10 of FIGS. 1 and 2. Output port 22 of bed 10 of FIGS. 3 and 4, however, is a ¼ inch jack receptacle as will be discussed in further detail below in connection with FIG. 7.

Referring now to FIGS. 5 and 6, the illustrative PROGRESSA® bed 10 shown therein has similar features as the illustrative VERSACARE® bed 10 of FIGS. 3 and 4 as well as the bed 10 of FIGS. 1 and 2. Thus, like reference numbers are used to denote like portions of these beds 10 and the descriptions above are equally applicable except where noted below in the discussion of bed 10 of FIGS. 5 and 6. In FIG. 5, the foot rail 46 at the left side of the bed 10 has been removed so that certain aspects of mattress support deck 30 are more readily visible. Bed 10 of FIG. 5 has a base 40' that includes a shroud and the metal frame members of the base frame covered by the shroud. The arms or links 41 of the lift system of bed 10 of FIG. 5 can also be seen, although the linear actuators that are operated to move arms 41 to raise, lower and tilt upper frame 38 relative to base 40' are covered by the shroud of base 40'.

Deck 30 of FIGS. 5 and 6 has flat panels for its various sections and so is not a step deck. Deck 30 of FIGS. 5 and 6 has a first head section portion or panel 32a and a second head section portion or panel 32b that are included in head section 32 of bed 10. As head section 32 is pivotably raised relative to upper frame 38, deck panel 32a translates in parallel relation with deck panel 32b in a direction indicated by arrow 82 in FIG. 5. As head section 32 is pivotably lowered relative to upper frame 38, deck panel 32a translates in parallel relation with deck panel 32b in a direction opposite of arrow 82. First antenna 13 of incontinence detection system 2 of FIGS. 5 and 6 is coupled to the movable deck panel 32a in a lower left side corner region thereof. Thus, antenna 13 translates with head section portion 32a relative to head section portion 32b. Cable 23 that extends from antenna 13 to reader 12 includes sufficient slack to accommodate this movement of antenna 13.

In some embodiments, a pivot axis about which head section 32 of bed 10 of FIGS. 5 and 6 pivots relative to upper frame 38 translates toward the head end of upper frame 38 when head section 32 is raised and translates toward the foot end of upper frame 38 when head section 32 is lowered. Such movement of the head section pivot axis during raising of head section 32 further increases a distance between antenna 13 and reader 12 which also is accommodated by slack in the respective cable 23. Additional details of a suitable mechanism for translating head section portion 32a relative to head section portion 32b and for translating the head section pivot axis relative to upper frame 38 can be found in U.S. Pat. No. 8,516,634 which is hereby incorporated by reference herein in its entirety. Further details of bed 10 of FIGS. 5 and 6 can also be found in *Service Manual, Progressa™ Bed, From Hill-Rom, Product No. P7500*, © 2013 by Hill-Rom Services, Inc.

A seat section 33 of deck 30 of bed 10 can be seen in FIGS. 5 and 6. Seat section 33 is situated longitudinally between the foot end of portion 32b of head section 32 and the head end of thigh section 34. Deck 30 of FIGS. 5 and 6 includes a pair of side panels 35, each of which is situated laterally outboard of seat section 33 and thigh section 34. Thus, one of panels 35 is located to the right of deck sections 33, 34 and the other of panels 35 is located to the left of deck sections 33, 35. Panels 35 and seat section 33 are fixed relative to upper frame 38 in the illustrative embodiment. Thus, in the lateral dimension of bed 10 of FIGS. 5 and 6, seat and thigh sections 33, 34 are not as wide as head and foot sections 32, 36. Accordingly, antenna 16 mounted to thigh section 34 of FIGS. 5 and 6 is located further from the left side of bed 10 than is antenna 13. The same can be said for antennae 14, 15 that are mounted to seat section 33. That is antennae 14, 15, 16 are located at different distances from the left side of bed 10 (or the left side of deck 30) of FIGS. 5 and 6 as compared to antenna 13. On seat section 33, antenna 14 is closer to the left side than is antenna 15. As discussed above, the placement of antennae 13, 14, 15, 16 on deck 30 is a matter of trial and error. In alternative embodiments, one or more of antennae 13, 14, 15, 16 are mounted to panel 35.

In the illustrative example of FIGS. 5 and 6, cables 23 are all routed from respective antennae 13, 14, 15, 16 to reader 12 through a space or gap 70' formed adjacent to a junction between the panel 35 at the left side of bed 10, a left head end corner region of seat section 33, and a left foot end corner region of panel 32b of head section 32. In the illustrative example of FIGS. 5 and 6, reader 12 is mounted to an undersurface of a longitudinal frame member 86 of upper frame 38. In other embodiments, reader 12 is mounted to a side surface of frame member 86. The side surface of frame member 86 in such embodiments may be the inwardly facing side surface (i.e., the one facing toward a center of bed 10) or the outwardly facing side surface (i.e., the one that can be seen in FIG. 5 facing away from the center of bed 10).

Foot section 36 of bed 10 of FIGS. 5 and 6 is also extendable and retractable. Thus, cable 25 shown in FIG. 5 has sufficient slack to accommodate the extension and retraction of foot section 36. Output port 22 of FIG. 5 is mounted to upper frame 38 to be raised, lowered, and tilted therewith. Thus, extra slack does not need to be provided in that cable 27 of FIG. 5 that extends between reader 12 and output port 22. Thus, in FIG. 5, cable 27 is shown as being situated against the inwardly facing side surface of upper frame member 86 along a majority of its length.

Referring now to FIG. 7, a diagrammatic view of bed 10 and incontinence detection system 20 is provided. Bed 10 of FIG. 15 has a mattress 100 (aka a patient support surface or just a surface) supported on deck sections 32, 33, 34, 36 of deck 30. Incontinence detection pad 60 having an RFID tag 64 is situated between a patient and mattress 100. Pad 60 is generally located beneath the patient's buttocks and upper thighs so as to increase the likelihood of absorbing and detecting incontinence expelled by the patient.

A head section motor 90 for pivotably raising and lowering head section 32 and a thigh section motor 92 for pivotably raising and lowering thigh section 34, such as through flanges, brackets, and/or linkages attached to frame 38 and sections 32, 34, are shown diagrammatically in FIG. 7. Motors 90, 92 are included in respective linear actuators in some embodiments of bed 10. Bed control circuitry 72 commands operation of motors 90, 92 in response to user inputs on bed as is known in the art.

As indicated diagrammatically in FIG. 7, antenna 16 is located a first distance $d_1$ away from RFID tag 64, antenna 15 is located a second distance $d_2$ away from RFID tag 64, antenna 14 is located a third distance $d_3$ away from RFID tag, and antenna 16 is located a fourth distance $d_4$ away from RFID tag 64. One of antennae 13, 14, 15, 16 are established as a transmit antenna that is controlled by reader 12 to emit energy through mattress 100 to RFID tag 64 and tag 64 responds with its data back through mattress 100 to another one of antennae 13, 14, 15, 16 which is established as a receive antenna. Reader 12 is also able to write data to RFID tag 64 via the established transmit antennae 13, 14, 15, 16. Thus, once pad 60 becomes wet a particular bit of data is set in memory of RFID tag 64 (more particularly, an RFID chip of tag 64) and when reader 12 processes the data received from RFID tag 64, it is able to determine whether the pad 64 is wet or not wet (more particularly, not sufficiently wet to cause the particular bit to get set).

If reader 12 determines that pad 60 is wet, a second bit (aka a kill bit) is set in RFID tag 64 by reader 12 via the established transmit antennae 13, 14, 15, 16. Once the kill bit is set in RFID tag 64, it remains unchanged thereafter. If pad 60 dries out after having been wet, reader 12 will see that the kill bit is still set when it receives subsequent data from RFID tag 64 such that the particular pad 60 should not be re-used. In some embodiments, reader 12 sends an alert to indicate that the pad 60 is a "bad" pad that should not be used because it has been previously soiled with wetness. In other embodiments, reader 12 simply causes visual indicator 18 to emit white light indicating that a "good" pad is not being read by the reader 12.

If desired, caregivers may place multiple pads 60 on mattress 100 beneath the patient. For example, it is not uncommon for two pads 60 to be used to increase the area of incontinence absorption beneath a patient. The reader 12 is able to read backscattered data from multiple RFID tags 64 of multiple pads 60 according to this disclosure. Some transmit/receive antennae combinations, for example, may read one RFID tag 64 and other transmit/receive antennae combinations may read another RFID tag 64, for example. Some transmit/receive antennae combinations may read multiple tags 64. Reader 12 initiates an alert, as described elsewhere herein, if any one or more of the multiple incontinence detection pads 60 indicate that they are wet.

As further indicated diagrammatically in FIG. 7, reader 12 has wireless communication capability. In the illustrative example, reader 12 communicates wirelessly with a wireless access point 118. The wireless communication between reader 12 and wireless access point 118 is bidirectional in some embodiments. That is, wireless messages can be sent and received by reader 12 and by wireless access point 118. Wireless access point 118 is coupled to a network 120 so that messages from reader 12 received by wireless access point 118 are ultimately able to be transmitted through network 120 to other computer devices of other systems. For example, messages from reader 12 are communicated to a nurse call system 122 in the illustrative example. The block 122 labeled nurse call system in FIG. 7 is intended to represent the various servers, computers, room stations, staff stations, and master nurse stations as well as any additional associated infrastructure associated with a nurse call system. Such nurse call systems and associated infrastructure are shown and described, for example, in U.S. Pat. Nos. 9,411, 934 and 8,598,995 which are hereby incorporated by reference herein.

As shown diagrammatically in FIG. 7, output port 22 is electrically coupled via a wired connection 124 to an input port 126 located on a wall 128 in a hospital room. In some embodiments, wall 128 may comprise a room wall of a healthcare facility. In other embodiments, wall 128 may comprise a panel of a piece of architectural equipment such as a headwall unit, a bed locator unit, a column, an arm, a service chase or the like that are installed in a hospital room. Input port 126 is coupled to network 120 via suitable infrastructure such as cabling, routers, gateways, and the like. Thus, data from reader 12 of system 20 communicated to port 126 from port 22 also can be received by computer devices of other systems such as nurse call system 122. Thus, in the illustrative example, reader 12 is able to communicate data from system 20 via a wired datalink 124 and a wireless datalink between reader 12 and wireless access point 118.

In some embodiments contemplated herein, reader 12 of incontinence detection system 20 is equipped with an 802.11 wireless communication capability for communication with wireless access point 118 which is, in turn, connected via network 120 to a remote computer or server of a Clinical Workflow Solutions (CWS) medical data management system 122. CWS system 122 may or may not be included as part of nurse call system 122. Block 122 in FIG. 7 is intended to represent CWS system either individually or collectively with the nurse call system. In such embodiments, reader 12 send the tag identification (ID) and an encrypted ID, both of which are received by reader 12 from tag 64 of pad 60, to the CWS system 122 for remote validation of the pad 60 placed on the bed 10. If more than one pad 60 is on bed 10, then reader 12 receives more than one tag ID and more than one encrypted ID. The CWS system 122 then performs decryption remotely and compares the tag ID and the data derived from decrypting the encrypted ID from the tag 64 to complete the validation. If desired, the data sent from the reader 12 is protected against transmission errors corrupting the data with standard Internet Protocol error checking algorithms and/or additional error detection could be applied by the reader 12 at the bed 10.

By moving the validation operation to a remote site, such as a computer of CWS system 122, having internet connectivity results in a number of advantages. Firstly, the processor of reader 12 at the bed 10 may not have the computational resources either in terms of memory or CPU cycles to accomplish the decryption locally. Secondly, the encryption algorithm can be changed at will and the algorithm used determined by tag ID so the deployment in the field is seamless. The encryption details and private keys may be managed by an online connection to a secure server at another facility (e.g., a server at the entity which manufactures or sells system 20 and/or bed 10), which enables the modification of the private key on an as-needed basis, a periodic change in private key or the wholesale replacement of the encryption algorithm in a secure fashion. In this way, the data generated for pad validation is done in an entirely secure fashion, and may be done on an as needed basis. If it is detected that the private key has become compromised, a new private key may be instituted and the pad serial numbers/private key maintained in a database at the CWS server 122 for pad validation.

The present disclosure also contemplates embodiments in which each incontinence detection pad 60 has the same unique authentication code stored in the respective RFID tag 64. One example of such a unique authentication code is the electronic product code (EPC) that is established by EPCglobal Inc. according to the EPCglobal Tag Data Standard. Thus, each RFID tag 64 of each pad 60 that is authorized for use in the incontinence detection system 20 will have stored in its memory the same authentication code (hereinafter referred to as "EPC"). In response to the RFID tag 64 of pad 60 being energized or scanned by the reader 12, the EPC is transmitted to the reader 12 from the RFID tag 64 as backscattered data along with other data such as data indicating whether the pad 60 is dry (e.g., unsoiled) or wet (e.g., soiled) and, in some embodiments, along with the tag ID. Prior to being assembled into pad 60, the RFID chip of tag 64 may have its own EPC in some embodiments. In such embodiments, the EPC of the RFID chip is overwritten with the pad-specific EPC during the manufacturing process of the pad 60. The overwriting of the EPC may occur before or after the RFID tag 64 is attached to one of the layers, such as backsheet 200, of pad 60 during manufacture. In use thereafter, the RFID tag 64 includes the pad-specific EPC in any responses it sends to reader 12.

If the reader 12 receives a transmission that does not include the pad-specific EPC that it should receive to indicate that an authorized pad 60 is being read by the reader 12, then the reader 12 ignores the transmission (which is referred to herein as an "unauthorized transmission") after making the determination that the EPC received from the RFID tag does not match the pad-specific EPC. Thus, by ignoring the unauthorized transmission, no message regarding the wet or dry status of an unauthorized pad is output by the reader 12. In some embodiments, however, the reader 12 may transmit or output other messages regarding the attempted use of an unauthorized pad in system 20 as will be further discussed below.

To make the determination as to whether a pad 60 is authorized or unauthorized, the reader 12 also has stored in its memory the pad-specific EPC for comparison purposes to the data received from the RFID tag 64. In some embodiments, if the reader 12 receives an unauthorized transmission, a warning message is transmitted from the reader 12 for display on bed 10 and/or on a device (e.g., master nurse station computer, room station, staff station, caregiver phone, pager, etc.) of nurse call system 122 and/or on some other device (e.g., smart phone, computer, etc.) included in, or accessible by, the network of the healthcare facility to notify one or more caregivers that an unauthorized pad is being used on bed 10. In some embodiments, the notification includes instructions to replace the unauthorized pad with an authorized pad 60.

If desired, the warning message from reader 12 regarding the use of an unauthorized pad on bed 10 is also transmitted to the manufacturer and/or seller of authorized pads 60. The manufacturer and/or seller of authorized pads 60 is then able to contact the healthcare facility regarding its use of unauthorized pads and to prompt the purchase of authorized pads 60. Optionally, the warning message from the reader 12 regarding the use of an unauthorized pad on bed 10 results in a notification to personnel of the healthcare facility advising that any warranties relating to incontinence detection system 20 may potentially become void as a result of the attempted use of unauthorized pads 60 on bed 10. Such a notification from the reader 12 regarding warranty voiding may be displayed on bed 10 and/or the various devices noted above, and also may be sent, for example, directly to other personnel (e.g., purchasing, legal, etc.) of the healthcare facility via e-mail, text message, or the like.

It is further contemplated by this disclosure that a "select" function of RFID tags is used to prevent unauthorized transmissions to the reader 12. According to the select function, a requesting device, such as reader 12, has the ability to send out a broadcast transmission message (aka a "select broadcast") containing the pad-specific EPC to all nearby devices (e.g., those within reception range of reader 12). The receiving devices including RFID tags (or other similar communication circuitry with the select function) that do not have the pad-specific EPC stored therein will, thereafter, not respond to any requests from the requesting device (e.g., reader 12) either indefinitely or for a threshold amount of time. Thus, by having the reader 12 transmit the select broadcast out with the pad-specific EPC, only authorized pads 60 with the pad-specific EPC stored therein will respond to subsequent requests from the reader 12, for at least the threshold time duration and/or until another select broadcast is transmitted to reset the threshold time.

It should be understood that use of authentication codes in incontinence detection pads, as just described above, may be used in any of the embodiments of incontinence detection pads described herein. Other examples of incontinence detection pads in which authentication codes may be used according to this disclosure can be found in U.S. Patent Application Publication Nos. 2018/0021184 A1; 2017/0246063 A1; 2017/0065464 A1; 2016/0374626 A1; and 2014/0276504, and in U.S. Provisional Application No. 62/660,558, filed Apr. 20, 2018, each of which is hereby incorporated by reference herein in their entirety for all that they teach to the extent not inconsistent with the present disclosure which shall control as to any inconsistencies.

System 20 and bed 10 may be used in home healthcare and other markets outside a traditional hospital or other healthcare facility. For such markets, the reader 12 may be constructed with a very limited functionality microprocessor by having the high compute resource intensity operations, such as decryption algorithms, accomplished remotely via any available internet connection. As a collateral benefit, a service is contemplated to automatically bill and send more incontinence pads to a customer (via prior arrangement), thereby enabling e-commerce business using existing hardware connections. Thus, a server of CWS system 122 or a server at a remote facility may perform pad usage data collection, may perform billing functions, and/or may generate inventory management data, as well as provide other notifications to hospitals or home users about incontinence detection pad 60 usage. For example, such usage data may include number of pads 60 used per day, week, and/or month; average amount of time before a dry pad becomes soiled; average amount of time after soiling before the wet pad is removed and/or replaced with a dry pad; and number of pads remaining from prior shipment quantity for usage.

In some embodiments, such as the illustrative embodiments of FIGS. 3, 5, and 7, output port 22 comprises a female ¼ inch receptacle which is configured for receipt of a male ¼ inch jack (sometimes referred to as a phono jack). Input port 126 is also a female ¼ inch receptacle that receives a male ¼ inch jack in some embodiments. In such embodiments, the data communicated via such ¼ inch receptacles and ¼ inch jacks are binary in nature to indicate simply whether incontinence detection pad 60 is wet or not wet. Such binary signals are sometimes referred to as contact closures because, when in a high state (e.g., logic level 1), they close a relay coupled to port 126 which, in turn, sends a signal to nurse call system 122. In some embodiments, the closure of the relay occurs at the low sate (e.g., logic level 0) rather than the high state depending upon the relay design. In either case, the signal to nurse call system 122 is a simple on/off or binary signal. In some embodiments, the relays are wired directly into the nurse call system 122 without involving network 120. If desired, a more sophisticated output port 22 and input port 126 may be used. For example, RJ-45 connectors, 37-pin connectors, RS-232 connectors and the like (e.g., multi-pin/multi-port or multi-contact) devices may be used as ports 22, 126 in some embodiments according to this disclosure.

In some embodiments, reader 12 energizes antennae 13, 14, 15, 16 to scan for RFID tag 64 using a linear frequency hopping scheme that cycles through fifty frequencies between a lower frequency limit and an upper frequency limit. In some embodiments, the lower frequency limit is about 902 Megahertz (MHz) and the upper frequency limit is about 928 MHz. The frequency hopping scheme is nonconsecutive and the hops are arranged in groups of five that start near the bottom of the frequency band and hop in approximately 5 Megahertz (MHz) jumps to near the top of the frequency band, then the hops go back near the bottom of the frequency band until all fifty frequencies are used. No frequency is used twice until all fifty frequencies have been used, at which time the sequence restarts. In some embodiments, the sequence of frequencies is as follows: 902.75; 907.75; 912.75; 917.75; 922.75; 906.75; 911.75; 916.75; 921.75; 926.75; 904.75; 909.75; 914.75; 919.75; 924.75; 903.25; 908.25; 913.25; 918.25; 923.25; 907.25; 912.25; 917.25; 922.25; 927.25; 905.25; 910.25; 915.25; 920.25; 925.25; 903.75; 908.75; 913.75; 918.75; 923.75; 905.75; 910.75; 915.75; 920.75; 925.75; 904.25; 909.25; 914.25; 919.25; 924.25; 906.25; 911.25; 916.25; 921.25; and 926.25. However, it should be appreciated that other sequences of fifty frequencies may be used in the frequency hopping scheme in other embodiments. In some embodiments, the sequence of fifty frequency hops is set arbitrarily by software.

As discussed above, each antenna 13, 14, 15, 16 is cycled through as being the transmit antenna and each of the remaining three antennae 13, 14, 5, 16 are cycled through as being the receive antenna. In this regard, the following twelve transmit and receive antenna combinations are provided in some embodiments: antenna 13 transmits and antenna 14 receives, followed by antenna 16 receives, followed by antenna 16 receives; antenna 14 transmits and antenna 13 receives, followed by antenna 15 receives, followed by antenna 16 receives; antenna 15 transmits and antenna 13 receives, followed by antenna 14 receives, followed by antenna 16 receives; and antenna 16 transmits and antenna 13 receives, followed by antenna 14 receives, followed by antenna 15 receives. In this scenario, there is only one transmit antenna and one receive antenna at any given instance during operation of reader 12. In each case, reader 12 uses the next available frequency in the hopping sequence when cycling through the transmit and the receive antennae combinations.

In the illustrative example, a multiple input multiple output (MIMO) antenna control scheme is not used because only one antenna transmits at any given time and only one other antenna is established as the receive antenna at any given time. However, it is within the scope of this disclosure for multiple output antennae (i.e., multiple transmit antennae that transmit substantially simultaneously) and/or multiple input antennae (i.e., multiple receive antennae that are established as receive antennae) to be established by reader 12 in other embodiments. For example, antennae 13, 14 may be established by reader 12 as transmit antenna and antennae 15, 16 may be established by reader 12 as receive antennae. All 2-by-2 combinations of antennae 13, 14, 15, 16 are contemplated. Alternatively, three of antennae 13, 14, 15, 16 may be established as transmit antennae and the remaining one antenna 13, 14, 15, 16 may be established as the receive antenna. All 3-by-1 combinations of antennae 13, 14, 15, 16 are contemplated. Further alternatively, one of antenna 13, 14, 15, 16 may be established as the transmit antennae and the remaining three antenna 13, 14, 15, 16 may be established as receive antennae. All 1-by-3 combinations of antennae 13, 14, 15, 16 are contemplated. In some embodiments, incontinence detection system 20 may have only three antennae or may have more than four antennae. All permutations and combinations of receive and transmit antennae designations are contemplated by this disclosure.

Figure 8:
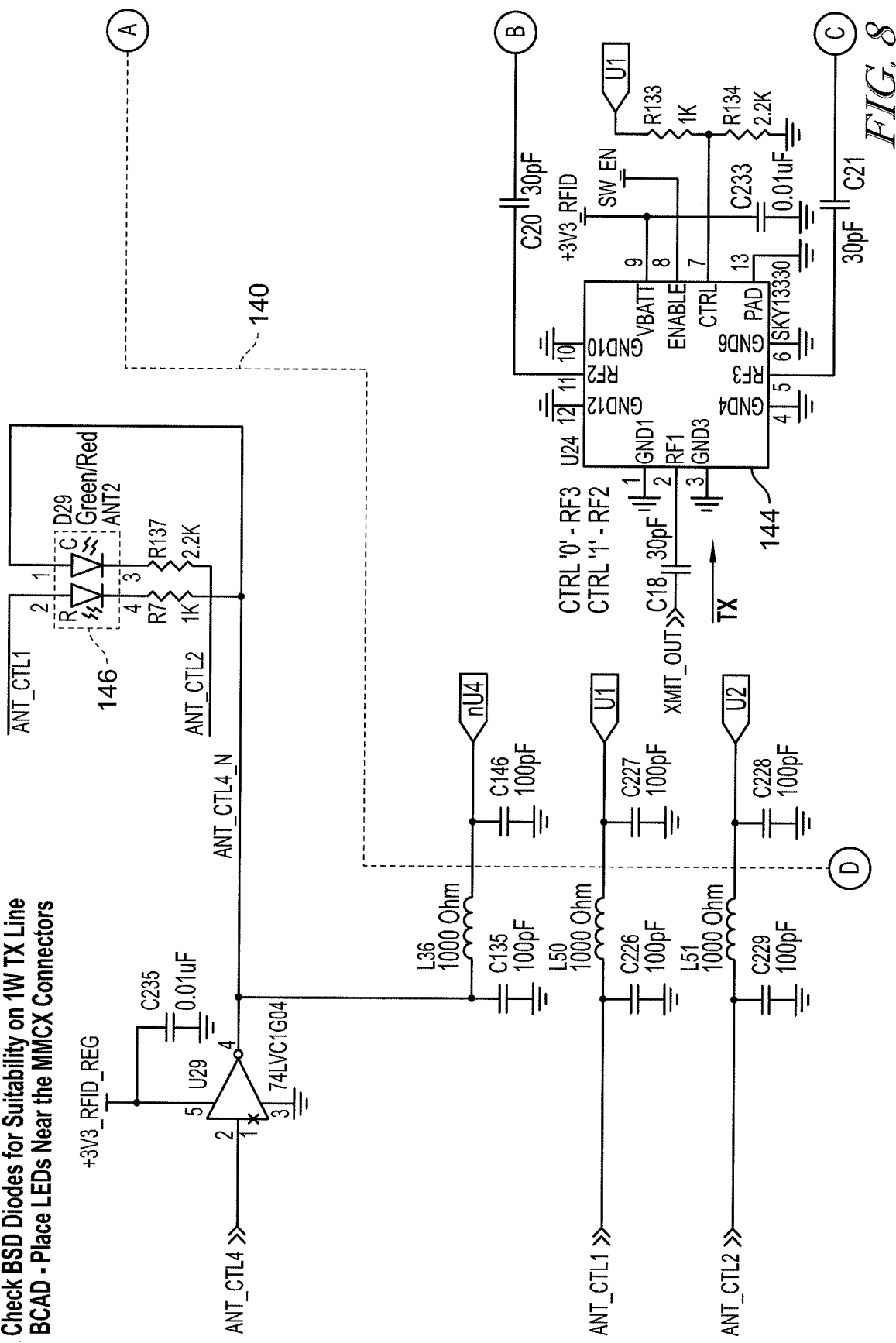
FIG. 8 (spanning four sheets) is an electric circuit schematic showing the reader including a bistatic radio frequency (RF) switch matrix that controls selection of the four antennae in various combinations for designating one of the four antennae as a transmitting antenna and designation another one of the remaining three antennae as a receiving antennae.
Figure 8:
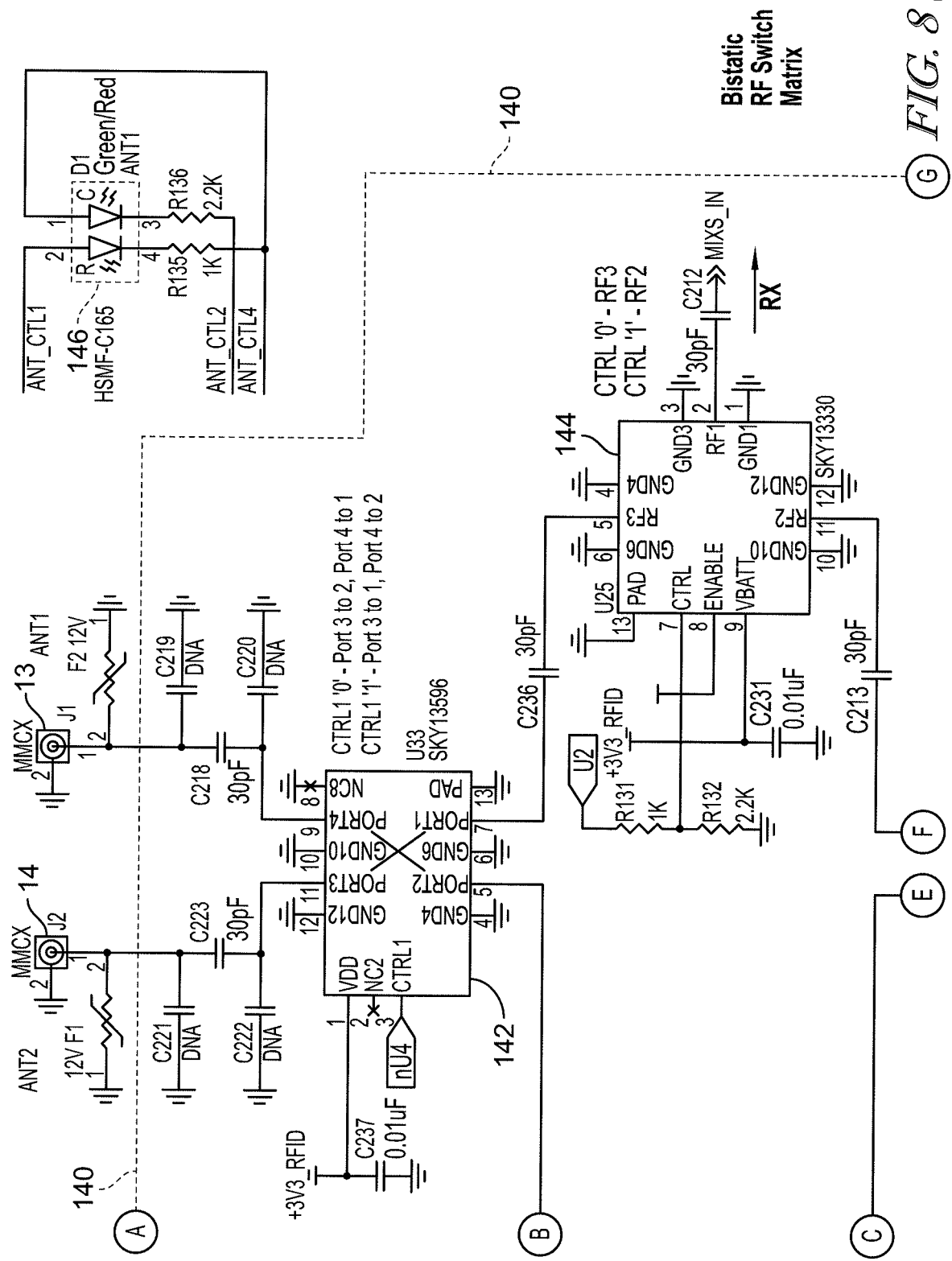
Figure 8:
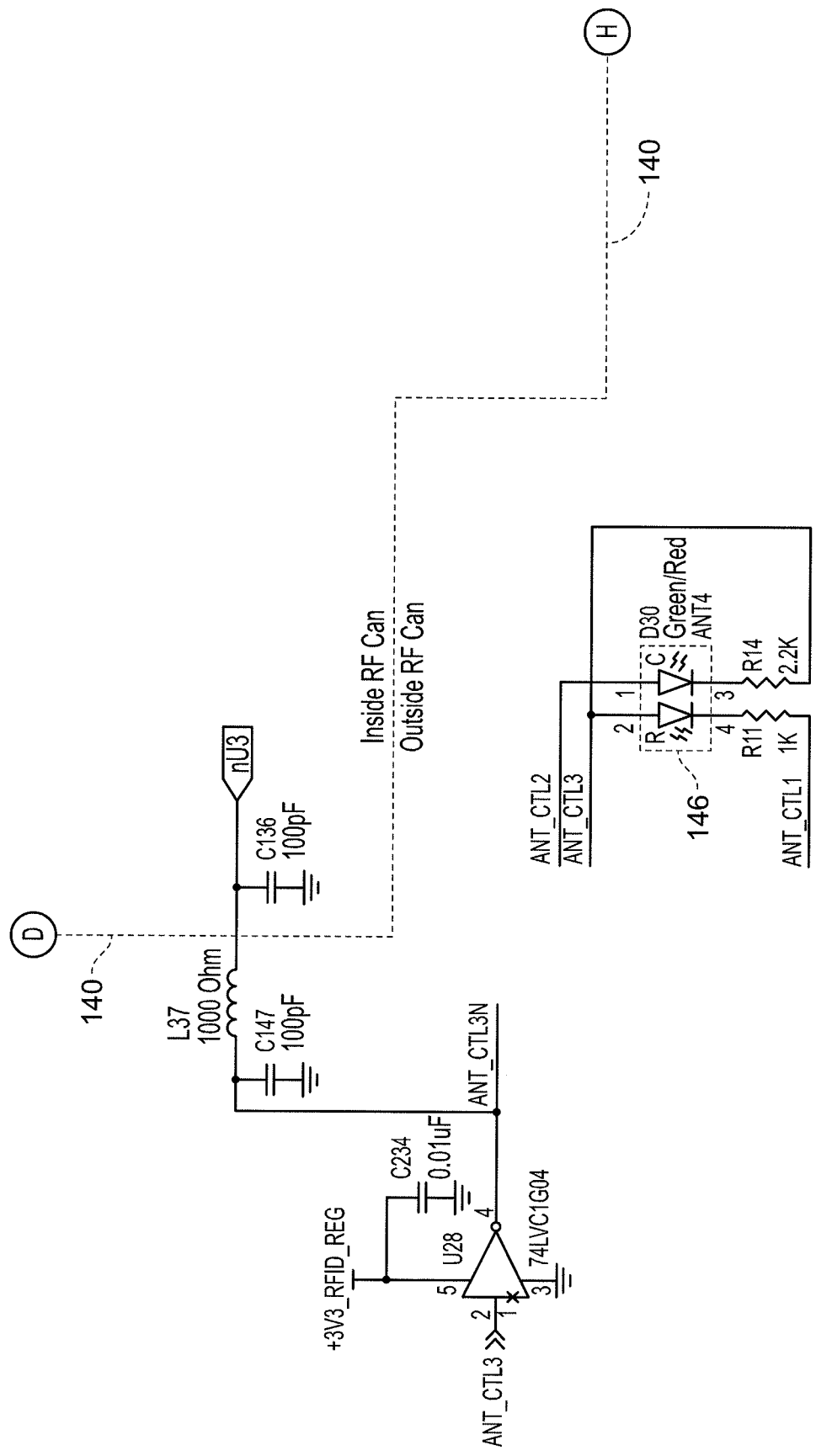
Figure 8:
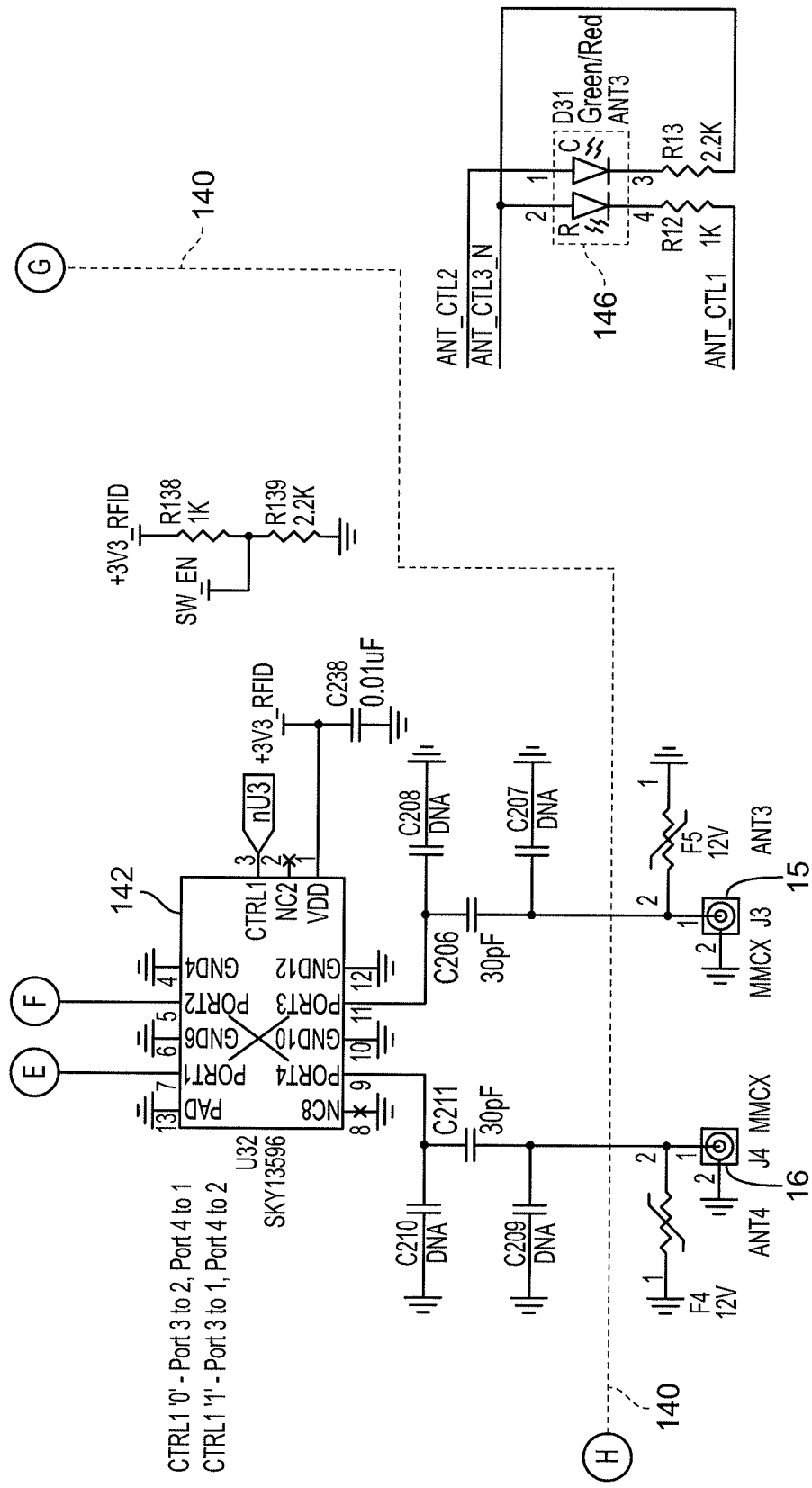

As shown in FIG. 8, which includes four pages, a portion of the circuitry of reader 12 includes a bistatic radio frequency (RF) switch matrix 140 which is used to select which antennae 13, 14, 15, 16 is the transmit antenna and which is the receive antennae. Other portions of the circuitry of reader 12 is shown and described in International Patent Application No. PCT/US2016/062167, particularly in connection with FIGS. 29A-C thereof. Illustrative bistatic RF switch matrix includes two model no. SKY 13596 double-pole, double-throw (DPDT) switches 142 and two model no. SKY 13330 single-pole, double-throw (SP2T) switches 144, each of which is available from Skyworks Solutions, Inc. of Woburn, Mass. The circuitry of FIG. 8 also includes a set of four HSMF-C165 miniature bi-color surface mount Chip-LED's 146 which each have a red diode and a green diode and which are available from Avago Technologies of San Diego, Calif. The red and green diodes of ChipLED's 146 are illuminated to indicate the operational status of the respective antenna 13, 14, 15, 16. For example, the green diode is illuminated when the respective antenna 13, 14, 15, 16 is operating as a transmit antenna or a receive antenna and the red diode is illuminated when the respective antenna 13, 14, 15, 16 is dormant and not being used as either a transmit or receive antenna. Further details of the circuitry associated with the bistatic RF switch matrix 140 are apparent in FIG. 8 and need not be discussed in detail.

According to this disclosure, the bistatic RF switch matrix 140 is operated in a full cycle scanning mode so that each of the first, second, third and fourth antenna 13, 14, 15, 16 is selectively chosen to be established as the transmit antenna and each of the remaining three antenna are selectively cycled through to be the receive antenna such that twelve transmit antenna and receive antenna combinations are operated. During the full cycle scanning mode, the transmit antenna and receive antenna combinations that produce valid reads of one or more RFID tags 64 of respective one or more incontinence detection pads 60 that are bed 10 are stored. In some embodiments, a modified cycle scanning mode is then determined for operation of the bistatic RF switch matrix 140 based on the valid reads such that only transmit antenna and receive antenna combinations that produced valid reads of the one or more RFID tags 64 are cycled through for a predetermined number of cycles, after which the bistatic RF switch matrix 140 is once again operated in the full cycle scanning mode.

The full cycle scanning mode may operate for several iterations so that, for example, ten reads of all possible antenna 13, 14, 15, 16 transmit/receive combinations are made before determining those combinations to be used in the modified cycle scanning mode. The predetermined number of iterations of the modified cycle scanning mode may be more or less than ten, for example. During the modified cycle scanning mode, the frequency hopping scheme described above continues to be used, just on a lesser number of transmit and receive antennae 13, 14, 15, 16 combinations. In some embodiments, if no valid reads of the passive RFID tag 64 are detected during the full cycle scanning mode, then the bistatic RF switch matrix 140 continues to operate in the full cycle scanning mode until at least one valid read is detected, after which the bistatic RF switch matrix 140 is operated in the modified cycle scanning mode.

Antennae 13, 14, 15, 16 of reader 12 are operated at low power (e.g., less than or equal to 1 Watt) to meet U.S. Federal Communications Commision (FCC) regulations for maximum permissible exposure (MPE) limits. The MPE limits specified by the FCC are dependent upon frequency and power density limits which are specified as an average value over a six minute period. In the 902 MHz-928 MHz frequency band, the power density limit is 0.601 milliWatts (mW)/cm² over any six minute period of time. In some embodiments, a delay period is provided between transmissions from antennae 13, 14, 15, 16 to keep within the MPE limits.

Figure 9:
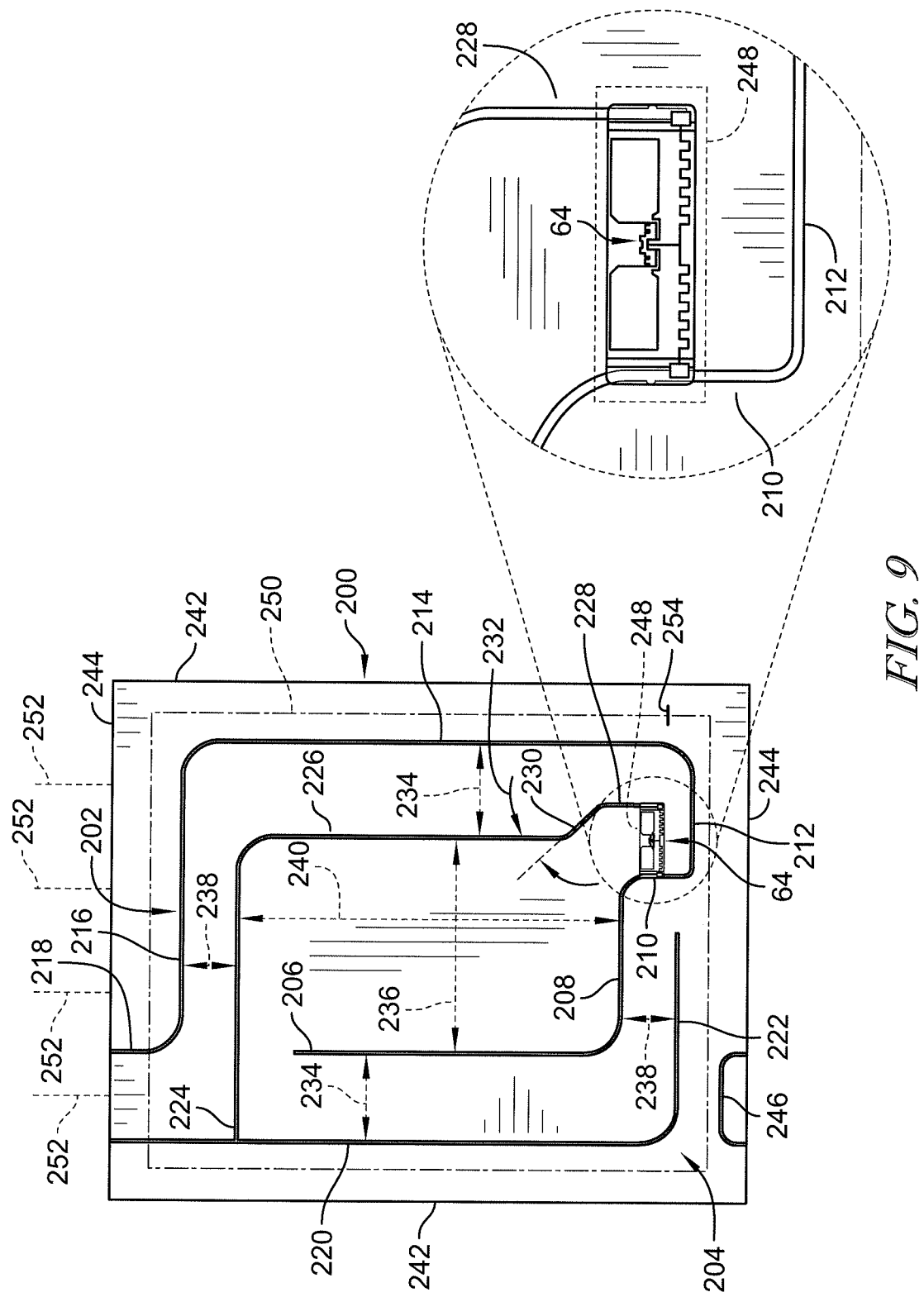
FIG. 9 is a top plan view of an electrical sheet of an incontinence detection pad of the incontinence detection system showing a pair of electrodes with respective ends terminating at a radio frequency identification (RFID) tag mounted on the electrical sheet and showing an enlarged bubble with the RFID tag attached to the electrical sheet within a rectangular tag footprint.

Referring now to FIG. 9, a backsheet 200 of an incontinence detection pad that is suitable for use with incontinence detection system 20 is shown. Backsheet 200 may replace the backsheets of any of the incontinence detection pad embodiments shown in International Application No. PCT/US2016/062167, such as those shown in FIGS. 8A-8D and 31-39, for example. Backsheet 200 is rectangular in shape and has first and second electrode traces 202, 204 printed thereon. Electrode traces 202, 204 are sometimes referred to herein as electrodes 202, 204.

Electrode 202 has a first straight line segment portion 206, a second straight line segment portion 208 that is substantially perpendicular to portion 206, a third straight line segment portion 210 which is substantially perpendicular to second portion 208 and which couples to RFID tag 64, a fourth straight line segment portion 212 that is substantially parallel with portion 208, a fifth straight line segment portion 214 which is parallel with portions 206, 210, a sixth straight line segment portion 216 which is parallel with portions 208, 212, and a seventh straight line segment portion 218 which is parallel with portions 206, 210, 214 and aligned with portion 206. The transitions between portions 206, 208, 210, 212, 214, 216, 218 are rounded such as having a radius of about 51.5 mm, although the radius between portions 208, 210 is about 36.5 mm and the radius between portions 210, 212 is even less than that. The rounded portions of trace 202 each extend over an arc of about 90°.

Electrode 204 has a first straight line segment portion 220, a second straight line portion 222 that is substantially perpendicular to portion 220, a third straight line segment portion 224 that extends from portion 222 in perpendicular relation therewith, a fourth straight line segment portion 226 that is substantially parallel with portion 220, a fifth straight line segment portion 228 that is substantially parallel with portion 226 and offset therefrom, and a sixth straight line segment portion 230 that, when extended, forms an included angle 232 of about 45° with portion 226. Portion 230 provides and inclined transition between portions 226, 228. Portion 228 also couples electrically with RFID tag 64. The transition between portion 220 and portion 222 and the transition between portion 224 and portion 226 is rounded over an arc of about 90° such as having a radius about 51.5 mm.

Portion 206 of trace 202 is substantially parallel with, and situated between, portions 220, 226 of trace 204. Portion 226 of trace 204 is substantially parallel with, and situated between, portions 206, 214 of trace 202. Similarly, portion 208 of trace 202 is substantially parallel with, and situated between, portions 222, 224 of race 204. Portion 224 of trace 204 is parallel with, and situated between, portions 208, 216 of trace 202. Electrodes 202, 204 are printed on backsheet 200 and comprise a conductive ink such as carbon ink, silver ink, or the like. In some embodiments, the thickness of traces 202, 204 is about 3.0 mm+/−0.5 mm.

Perpendicular distances 234 between portion 206 of electrode 202 and portion 220 of electrode 204 and between portion 214 of electrode 202 and portion 226 of electrode 204 is about 127.0 mm in the illustrative example. A perpendicular distance 236 between portion 206 of electrode 202 and portion 226 of electrode 204 is about 317.0 mm in the illustrative example. Thus, the distance 236 between portions 206, 226 is more than twice that of each of distances 234. In particular, the ratio of distance 236 to 234 is about 317/127=2.496.

Perpendicular distances 238 between portion 208 of electrode 202 and portion 222 of electrode 204 and between portion 216 of electrode 202 and portion 224 of electrode 204 is about 77.0 mm in the illustrative example. A perpendicular distance 240 between portion 208 of electrode 202 and portion 224 of electrode 204 is about 537.0 mm in the illustrative example. Thus, the distance 240 between portions 208, 224 is more than six times that of each of distances 238. In particular, the ratio of distance 236 to 234 is about 537/77=6.974.

Long side edges 242 of backsheet 200 have lengths of about 900.0 mm and short end edges 244 have lengths of about 750.0 mm in the illustrative example. The long dimension of backsheet 200 is sometimes referred to as the machine direction (MD) and the short dimension of backsheet 200 is sometimes referred to as the cross direction (CD). Distance 236 between the electrode segment portions 206, 226 is greater than 30% and greater than 40% of the 750.0 mm distance defined between the long sides 242 of the layer 200. In particular, the ratio of distance 236 to 750.0 mm is 317/750=0.423 or 42.3% on a percentage basis. Distance 240 between the electrode segment portions 208, 224 is greater than 40% and greater than 50% of the 900.0 mm distance defined between the short ends 242 of the layer 200. In particular, the ratio of distance 240 to 900.0 mm is 537/900=0.597 or 59.7% on a percentage basis.

Distances 236 between electrode portions 206, 226 and distance 240 between electrode portions 208, 224 provide the incontinence detection pad 60 having backsheet 200 with a relative large central region that is devoid of any electrode portions. This represents an improvement over the electrode trace geometry of the incontinence detection pad disclosed in International Patent Application No. PCT/US2016/062167, particularly in connection with FIG. 31 thereof. During testing, it was found that patients having a gel or ointment applied to the patient's buttocks and/or sacral region could cause an electrically conductive path to be formed between the electrode segments in the central region of the pad. The gel or ointment was conducting the electricity between the electrodes thereby causing false positives with regard to incontinence detection. Thus, spacing electrodes 206, 226 farther apart and spacing electrodes 208, 224 father apart than in the prior art pad, the chances of the gel or ointment on a patient closing the circuit between electrode traces 202, 204 is reduced significantly.

Backsheet 200 includes a sacrificial trace 246 in an end region adjacent to one of edges 244. Sacrifical trace 246 is left over from an electrode trace of a next adjacent backsheet 200 during a manufacturing process as is described in further detail in International Patent Application No. PCT/US2016/062167, particularly in connection with FIG. 36 thereof. Sacrificial trace 246 is somewhat U-shaped or C-shaped. An RFID tag foot print 248 in the form of a dashed rectangle is printed on backsheet 200 as shown in FIG. 9. Portion 210 of electrode 202 and portion 228 of electrode 204 extended into foot print 248 for coupling electrically to RFID tag 64. Foot print 248 delineates an alignment zone or region of backsheet 200 within which RFID tag 64 can be placed and form proper electrical contacts with portions 210, 228 of electrodes 202, 204. In FIG. 9, an enlarged bubble to right of backsheet 200 shows RFID tag 64 installed on backsheet 200 within the foot print 248.

Still referring to FIG. 9, a substantially rectangular phantom box 250 is shown on backsheet 200 to delineate the general location of a perimeter of an absorbent core of an incontinence detection pad 60 in which backsheet 200 is included. A set of dashed lines 252 adjacent one of edges 244 indicates the locations at which the incontinence detection pad having backsheet 200 is folded in the machine direction. It should be noted that the two fold lines 252 on the right side of backsheet 200 pass to the right and left of foot print 248 and the RFID tag 64 contained therein. Thus, the machine direction folds 252 are oriented so that the RFID tag 64 is not folded when the associated incontinence detection pad 60 is folded. Backsheet 200 also has an additional registration mark 254 that is used during the manufacture of the incontinence detection pad in which backsheet 200 is included.

Although certain illustrative embodiments have been described in detail above, variations and modifications exist within the scope and spirit of this disclosure as described and as defined in the following claims.

The invention claimed is:

1. An incontinence pad comprising:
an absorbent material;
an electrical sheet adjacent the absorbent material;
the electrical sheet comprising:
a layer of material shaped generally as a rectangle having first and second long sides and first and second short sides,
an RFID tag coupled to the layer closer to the first short side than the second short side, and
first and second electrodes on the layer and electrically coupled to the RFID tag, the first and second electrodes including first, second, third and fourth electrode segments that are generally parallel with the first and second long sides of the layer, the second and third electrode segments being situated between the first and fourth electrode segments, the second and third electrode segments being spaced apart by a first distance that is at least twice a second distance defined between the first and second electrode segments and between the third and fourth electrode segments;
wherein the RFID tag includes a memory location, wherein an authentication code is stored in the memory location and is configured to cause a reading system to alert based on the detection of fluid; and
wherein the RFID tag includes a transmitter configured to transmit a signal indicating the presence of fluid, wherein the transmitter is further configured to transmit the authentication code.

2. The incontinence pad of claim 1, wherein the RFID tag comprises a passive RFID tag.

3. The incontinence pad of claim 1, wherein the authentication code comprises an electronic product code.

4. The incontinence pad of claim 1, wherein the layer of material comprises a fluid resistant backsheet layer.

5. The incontinence pad of claim 4, further comprising a fluid permeable topsheet layer.

6. The incontinence pad of claim 1, wherein the first and second electrodes comprise conductive traces.

7. The incontinence pad of claim 5, wherein the conductive traces comprise conductive ink printed on the layer of material.

8. An incontinence detection system comprising
an incontinence detection pad for placement beneath a person to be monitored, the incontinence detection pad including an electrical sheet comprising a layer of material shaped generally as a rectangle having first and second long sides and first and second short sides, an RFID tag coupled to the layer closer to the first short side than the second short side, and first and second electrodes on the layer and electrically coupled to the RFID tag, the first and second electrodes including first, second, third and fourth electrode segments that are generally parallel with the first and second long sides of the layer, the second and third electrode segments being situated between the first and fourth electrode segments, the second and third electrode segments being spaced apart by a first distance that is at least twice a second distance defined between the first and second electrode segments and between the third and fourth electrode segments, the RFID tag storing an authentication code which is common to all incontinence detection pads that are authorized for use in the incontinence detection system,
a reader having circuitry in which the authentication code is also stored, and
at least one antenna coupled to the reader, wherein the reader is operable to send a request to the RFID tag via the at least one antenna and to read via the at least one antenna data emitted from the RFID tag in response to the request, the reader is configured to confirm that the incontinence detection pad is an authorized incontinence detection pad by determining that the data received from the RFID tag includes the authentication code, wherein the reader is configured to transmit a message indicating that the authorized incontinence detection pad is wet if the data received from the RFID tag indicates that the incontinence detection pad is wet, wherein the reader does not transmit the message if the data does not include the authentication code.

9. The incontinence detection system of claim 8, wherein the authentication code comprises an electronic product code (EPC).

10. The incontinence detection system of claim 8, wherein the request to the RFID tag from the reader also includes the authentication code and the RFID tag only responds to the request if the authentication code is included in the request from the reader.

11. The incontinence detection system of claim 8, wherein the RFID tag comprises a passive RFID tag that emits the data as backscattered data.

12. The incontinence detection system of claim 11, wherein the backscattered data includes pad status data indicating whether the incontinence detection pad is dry or wet.

13. The incontinence detection system of claim 12, wherein the backscattered data further includes a tag identification (ID) for the passive RFID tag.

14. The incontinence detection system of claim 8, wherein the reader is configured to transmit a warning message if the data received from the RFID tag does not include the authentication code, the warning message comprising a notification indicating that an unauthorized incontinence detection pad is being used with the patient.

15. The incontinence detection system of claim 14, wherein the warning message is transmitted from the reader for display on a patient bed on which the patient is supported.

16. The incontinence detection system of claim 15, wherein the reader and the at least one antenna are coupled to the bed.

17. The incontinence detection system of claim 14, wherein the warning message is transmitted from the reader to at least one remote computer device.

18. The incontinence detection system of claim 17, wherein the at least one remote computer device comprises one or more of the following: a master nurse station, a room station, a staff station, a caregiver phone, a pager, a smart phone, or a computer.

19. The incontinence detection system of claim 14, wherein the warning message includes instructions to replace the unauthorized pad with an authorized pad.

20. The incontinence detection system of claim 14, wherein the reader is configured to transmit a notification regarding the use of an unauthorized pad with the patient to a manufacturer or a seller of authorized incontinence detection pads.

21. The incontinence detection system of claim 14, wherein the reader is configured to transmit a notification to personnel of the healthcare facility advising that any warranties relating to the incontinence detection system may potentially become void as a result of the attempted use of an unauthorized pad with the patient.

22. A method of manufacturing a plurality of incontinence detection pads, the method comprising
receiving a plurality of RFID tags each having a chip-specific electronic product code (EPC) code stored in a memory of the respective RFID tag,
overwriting the chip-specific EPC with a pad-specific EPC in each of the plurality of RFID tags such that each RFID tag has a common pad-specific EPC stored in its respective memory; and
coupling each RFID tag to a first layer of a plurality of layers of a corresponding one of the plurality of incontinence detection pads, wherein each incontinence detection pad of the plurality of incontinence detection pads includes an electrical sheet comprising a layer of material shaped generally as a rectangle having first and second long sides and first and second short sides, an RFID tag coupled to the layer closer to the first short side than the second short side, and first and second electrodes on the layer and electrically coupled to the RFID tag, the first and second electrodes including first, second, third and fourth electrode segments that are generally parallel with the first and second long sides of the layer, the second and third electrode segments being situated between the first and fourth electrode segments, the second and third electrode segments being spaced apart by a first distance that is at least twice a second distance defined between the first and second electrode segments and between the third and fourth electrode segments.

23. The method of claim 22, wherein overwriting the chip-specific EPC with the pad-specific EPC of each of the plurality of RFID tags occurs prior to the coupling of each RFID tag to the respective first layer.

24. The method of claim 22, wherein overwriting the chip-specific EPC with the pad-specific EPC of each of the plurality of RFID tags occurs after the coupling of each RFID tag to the respective first layer.

25. The method of claim 22, wherein the plurality of layers of each of the plurality of incontinence detection pads includes an absorbent layer and further comprising covering the RFID tag and at least a portion of the first layer of each incontinence detection pad with the respective absorbent material.

26. The method of claim 22, wherein coupling each RFID tag to the respective first layer comprises coupling each RFID tag to a respective pair of conductive electrodes supported by the corresponding first layer.

27. The method of claim 22, wherein the plurality of RFID tags comprises passive RFID tags.

28. The method of claim 22, wherein the first layer of each of the plurality of incontinence detection pads comprises a fluid resistant backsheet layer.

29. The method of claim 22, wherein the plurality of layers of each incontinence detection pad of the plurality of incontinence detection pads further comprises a fluid permeable topsheet layer.

* * * * *